(12) United States Patent
Nozaki et al.

(10) Patent No.: US 11,589,830 B2
(45) Date of Patent: Feb. 28, 2023

(54) INFORMATION PROCESSING APPARATUS, METHOD AND NON-TRANSITORY COMPUTER READABLE MEDIUM

(71) Applicants: OMRON HEALTHCARE CO., LTD., Muko (JP); OMRON Corporation, Kyoto (JP)

(72) Inventors: Daisuke Nozaki, Kyoto (JP); Hironori Sato, Kyoto (JP)

(73) Assignees: OMRON HEALTHCARE CO., LTD., Muko (JP); OMRON CORPORATION, Kyoto (JP)

( * ) Notice: Subject to any disclaimer, the term of this patent is extended or adjusted under 35 U.S.C. 154(b) by 412 days.

(21) Appl. No.: 16/710,324

(22) Filed: Dec. 11, 2019

(65) Prior Publication Data

US 2020/0113528 A1  Apr. 16, 2020

Related U.S. Application Data

(63) Continuation of application No. PCT/JP2018/022223, filed on Jun. 11, 2018.

(30) Foreign Application Priority Data

Jun. 19, 2017 (JP) .............................. JP2017-119991

(51) Int. Cl.
*A61B 5/021* (2006.01)
*A61B 5/00* (2006.01)
*G06F 17/18* (2006.01)

(52) U.S. Cl.
CPC .............. *A61B 5/746* (2013.01); *A61B 5/021* (2013.01); *A61B 5/742* (2013.01); *G06F 17/18* (2013.01)

(58) Field of Classification Search
CPC ......... A61B 5/746; A61B 5/021; A61B 5/742; G06F 17/18
See application file for complete search history.

(56) References Cited

U.S. PATENT DOCUMENTS

| 2016/0029970 A1* | 2/2016 | Park | A61B 5/0002 600/587 |
| 2016/0242700 A1* | 8/2016 | Ferber | A61B 5/681 |
| 2017/0319184 A1* | 11/2017 | Sano | A61B 5/4318 |

FOREIGN PATENT DOCUMENTS

| CN | 104997498 A * | 10/2015 | ............. A61B 5/021 |
| CN | 104997498 A | 10/2015 | |

(Continued)

OTHER PUBLICATIONS

Stergiou, George S., et al. "Self-monitoring of blood pressure at home: how many measurements are needed?." Journal of hypertension 16.6 (1998): 725-731. (Year: 1998).*

(Continued)

*Primary Examiner* — Navin Natnithithadha
*Assistant Examiner* — Meghan R Kumar
(74) *Attorney, Agent, or Firm* — Oliff PLC

(57) ABSTRACT

An information processing apparatus of the invention is configured to: determine whether or not first biological information of a measurement subject meets a first condition, the first biological information being measured in a first period; determine, when the first biological information meets the first condition, whether or not a number of times, by which the first biological information meets the first condition with respect to the measurement subject, exceeds a first value; select a first message when the first value is not exceeded; select a second message when the first value is exceeded.

12 Claims, 17 Drawing Sheets

(56) References Cited

FOREIGN PATENT DOCUMENTS

| JP | 2002-056099 A | 2/2002 |
|---|---|---|
| JP | 2004-164173 A | 6/2004 |
| JP | 2007-047929 A | 2/2007 |
| JP | 2013-183974 A | 9/2013 |
| JP | 2016-219018 A | 12/2016 |
| JP | 2018-64702 A | 4/2018 |
| WO | 2012/148044 A1 | 11/2012 |
| WO | 2016/087290 A1 | 6/2016 |

OTHER PUBLICATIONS

Shimamoto, K., Ando, K., Fujita, T., Hasebe, N., Higaki, J., Horiuchi, M., . . . & Umemura, S. (2014). The Japanese Society of Hypertension guidelines for the management of hypertension (JSH 2014). Hypertension Research, 37(4), 253-390. (Year: 2014).*

James et al., "2014 Evidence-Based Guideline for the Management of High Blood Pressure in Adults Report From the Panel Members Appointed to the Eighth Joint National Committee (JNC 8)", Clinical Review and Education, 2014, 311(5), pp. 507-520.

"JSH Guidelines for the Managament of Hypertension 2014", The Japanese Society of Hypertension, 2014, pp. i-236.

Aug. 7, 2018 International Search Report issued in International Patent Application No. PCT/JP2018/022223.

"The type of hypertension you want to be particularly careful about"; OMRON; Jun. 2017; <https://web.archive.org/web/20170606153704/http://www.healthecare.omron.co.jp:80/resource/guide/hightbp/04.html>.

Nov. 10, 2020 Office Action issued in Japanese Patent Application No. 2017-119991.

Nov. 17, 2021 Office Action issued in Chinese Patent Application No. 201880040812.5.

* cited by examiner

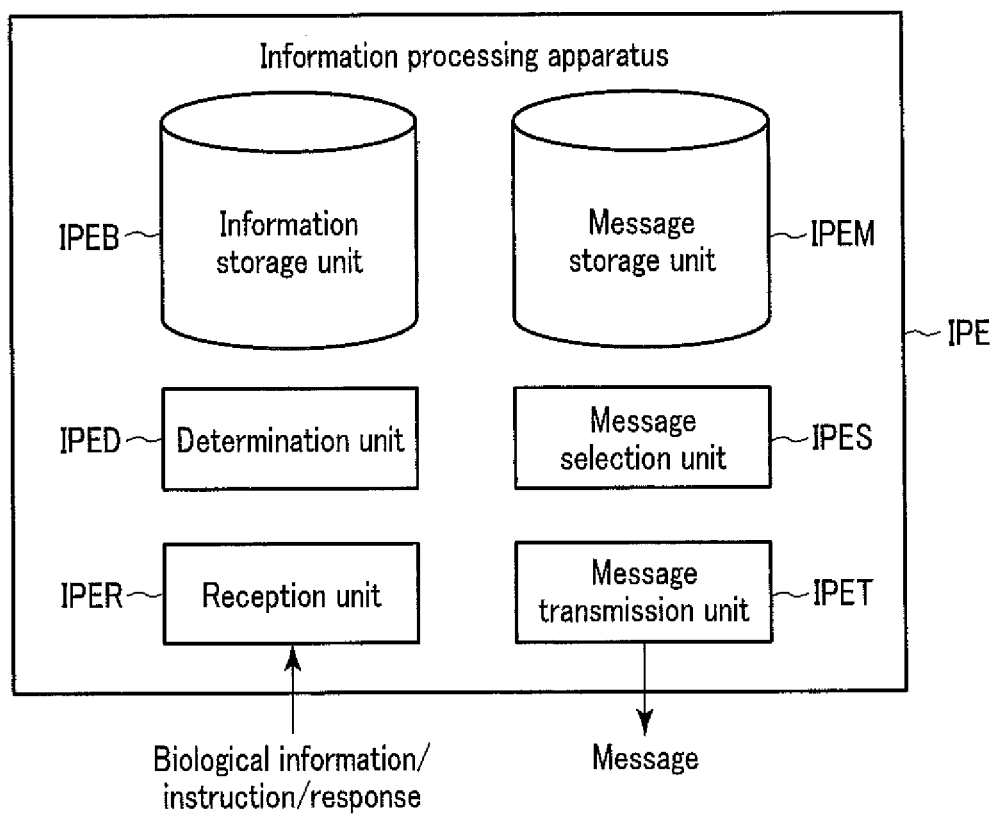
F I G. 1

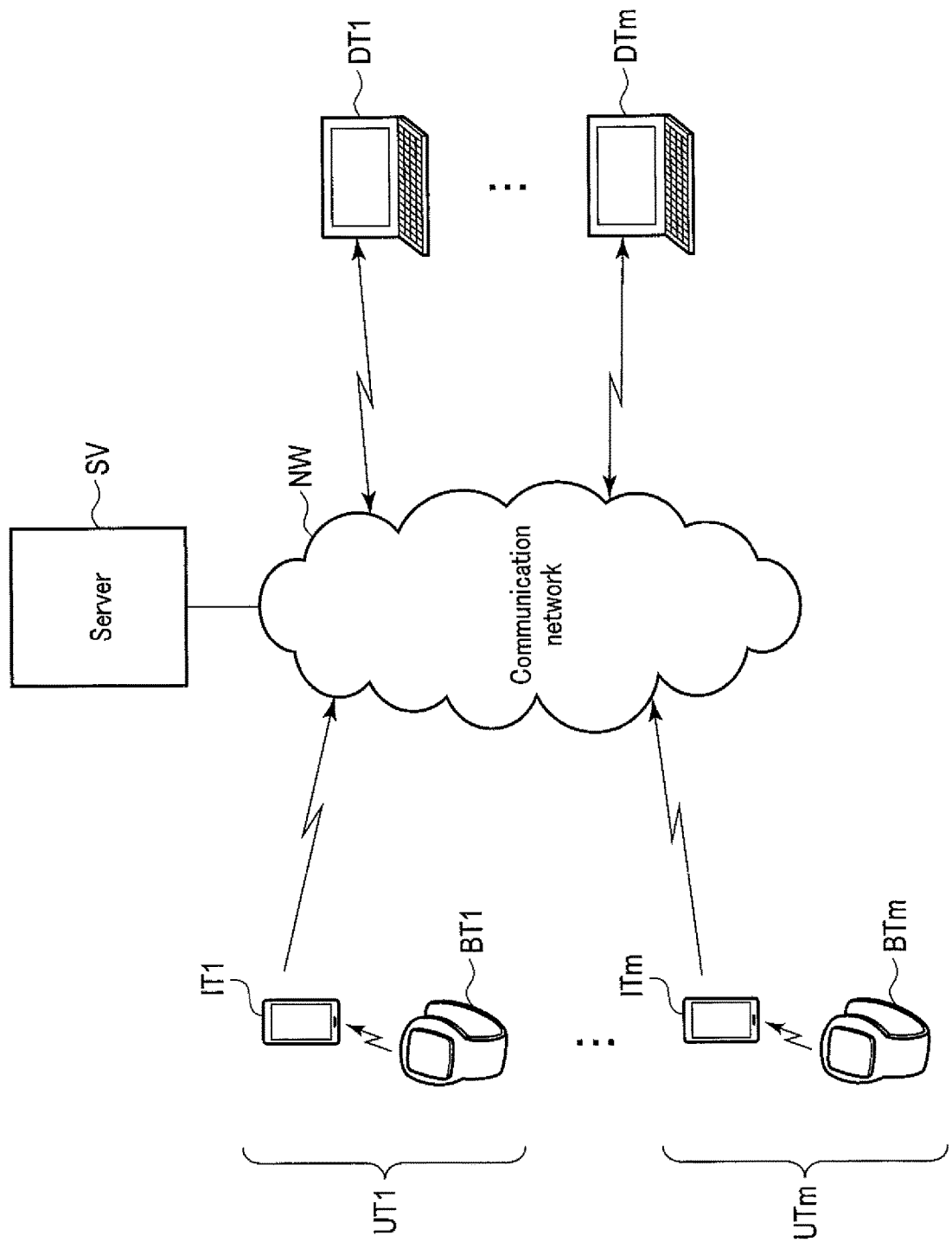
F I G. 2

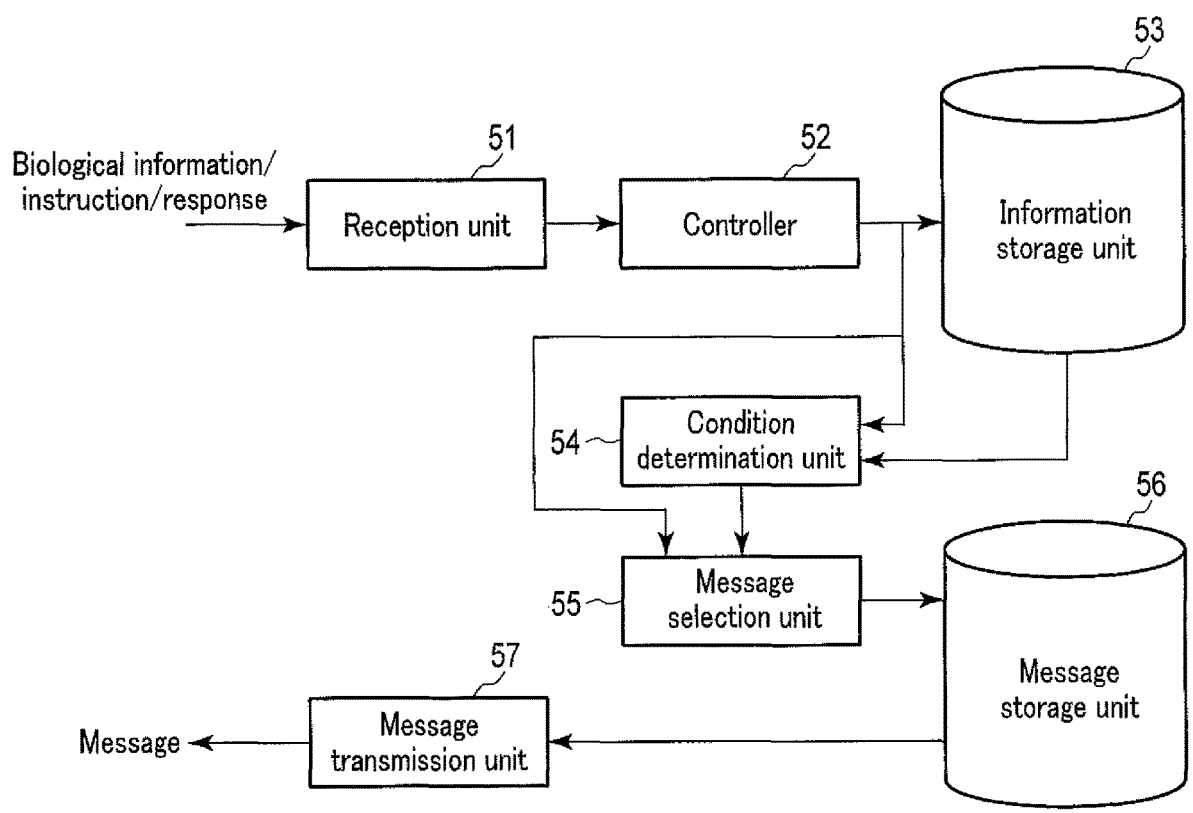
F I G. 7

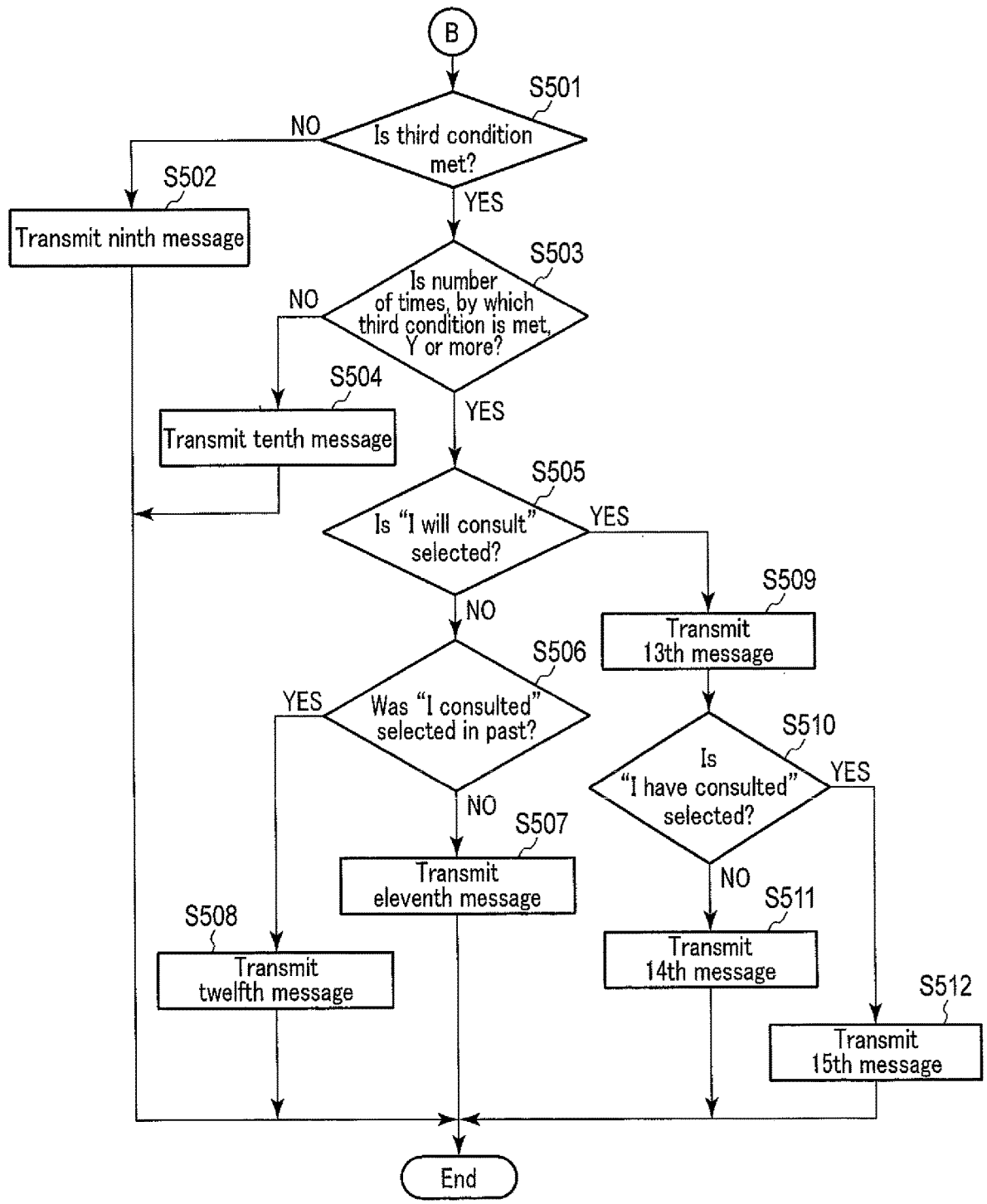
F I G. 12

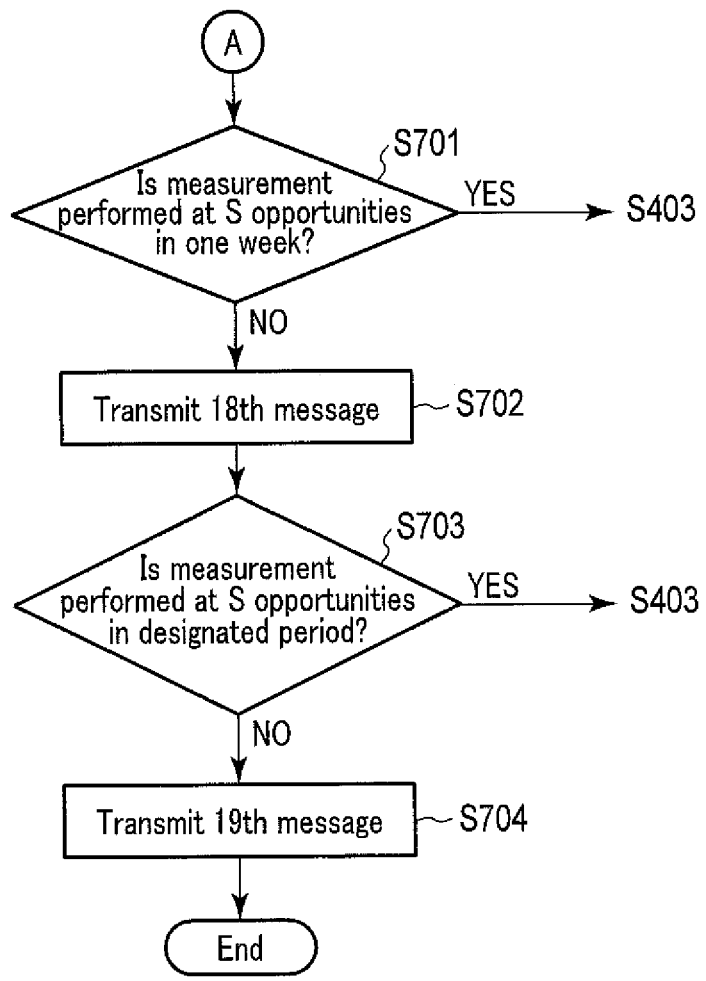
F I G. 14

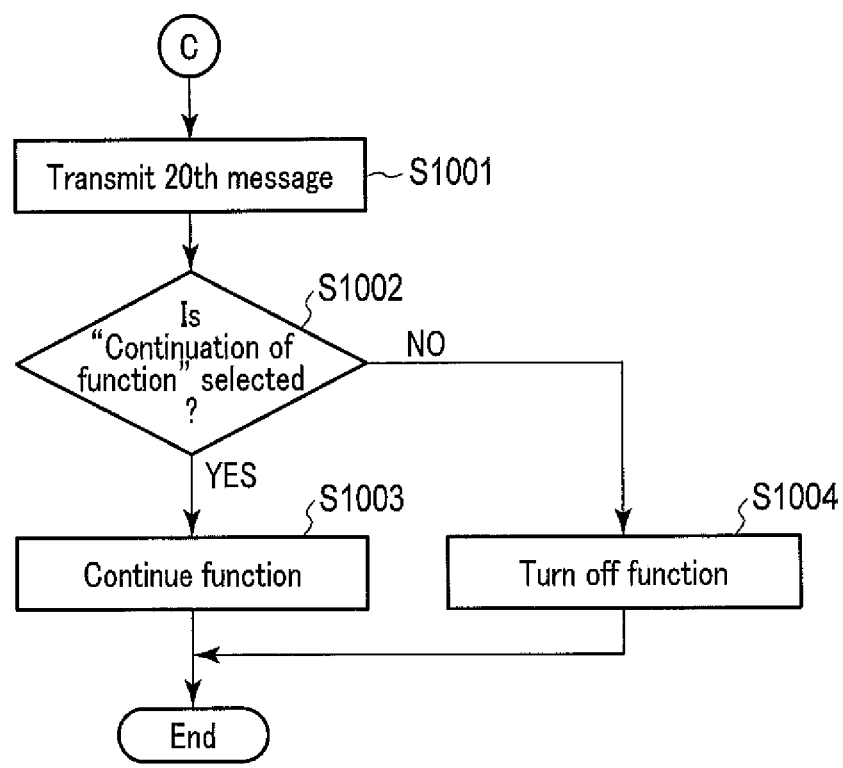
F I G. 17

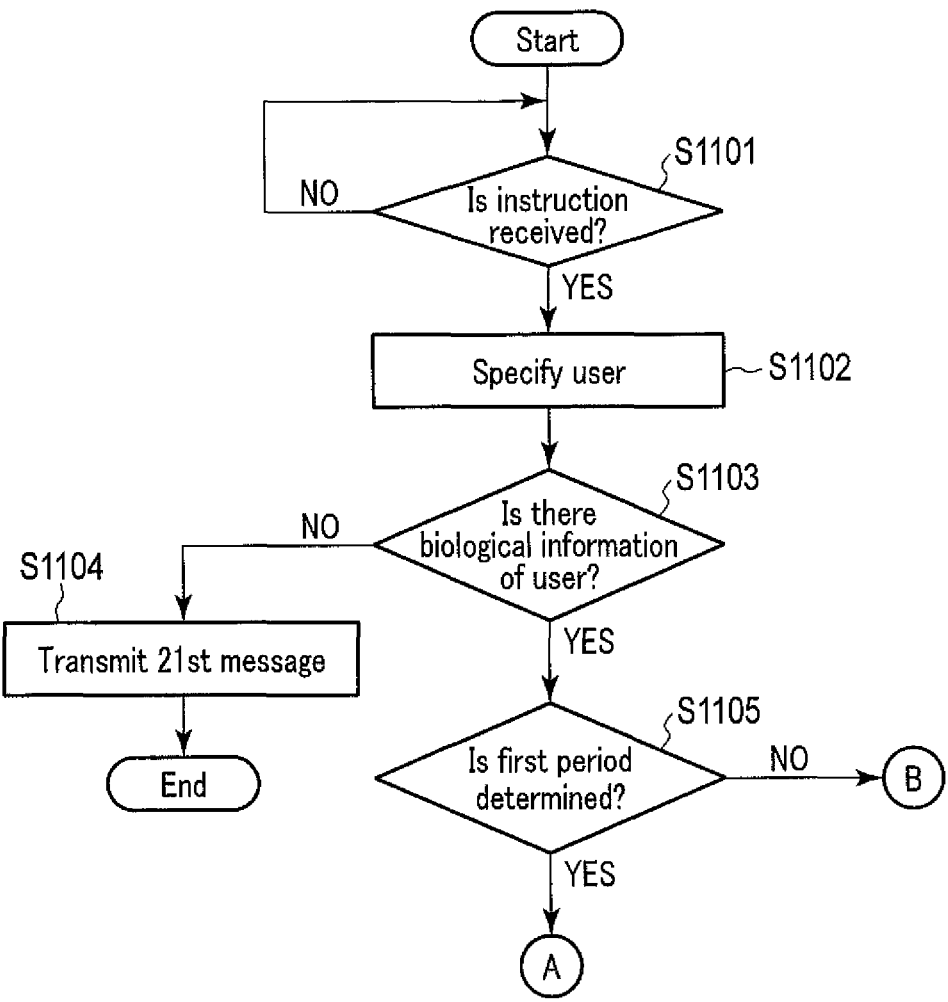
F I G. 18

INFORMATION PROCESSING APPARATUS, METHOD AND NON-TRANSITORY COMPUTER READABLE MEDIUM

CROSS-REFERENCE TO RELATED APPLICATIONS

This application is a Continuation Application of PCT Application No. PCT/JP2018/022223, filed Jun. 11, 2018 and based upon and claiming the benefit of priority from Japanese Patent Application No. 2017-119991, filed Jun. 19, 2017, the entire contents of all of which are incorporated herein by reference.

FIELD

The present invention relates to an information processing apparatus which processes a blood pressure value that is measured, a method, and a program.

BACKGROUND

In a treatment of hypertension, in general, a doctor prescribes antihypertensive medication to a patient, by taking into account a result of a medical examination. Guidelines are determined on methods of prescription. The doctor determines the content of prescription according to the guidelines, based on a medical history, a blood pressure value, a variation amount of a blood pressure value, etc. (see, for example, the Japanese Society of Hypertension (JSH) Guidelines for the Management of Hypertension 2014 (JSH2014), or James P A, Operil S, Carter B L, et al. "2014 Evidence-Based Guideline for the Management of High Blood Pressure in Adults" JAMA, 2014; 311: 507).

In addition, there is known a method of extracting, from a disease name of a lifestyle-related disease described on a statement of medical expenses, examination data of a medical examination relating to the disease name, performing calculation on the examination data and diagnostic criteria of respective medical societies, and determining necessity/nonnecessity of a consultation to a medical institution (see, for example, Jpn. Pat. Appln. KOKAI Publication No. 2004-164173).

SUMMARY

There is a case in which a person who takes care of his/her own health measures his/her blood pressure value in the home. However, in general, a measurement subject does not grasp guidelines (e.g. JSH Guidelines for the Management of Hypertension 2014). Thus, even if a measurement subject measures the blood pressure value by himself/herself, it is difficult for the measurement subject to judge by himself/herself whether or not to consult a medical institution, a medical specialist, or a lifestyle-related disease certified physician.

The present invention, in one aspect, has been made in consideration of the above circumstance, and the object of the invention is to provide a technology which makes it possible to support a measurement subject in judging by himself/herself whether or not to consult a medical institution, a medical specialist, or a lifestyle-related disease certified physician.

The present invention adopts the following configurations in order to solve the above-described problem.

Specifically, an information processing apparatus according to a first mode of the present invention is configured to: determine whether or not first biological information of a measurement subject meets a first condition, the first biological information being measured in a first period; determine, when the first biological information meets the first condition, whether or not a number of times, by which the first biological information meets the first condition with respect to the measurement subject, exceeds a first value; select a first message when the first value is not exceeded; select a second message when the first value is exceeded; determine whether or not second biological information of the measurement subject meets a second condition, the second biological information being measured in a second period which is different from the first period; determine, when the second biological information meets the second condition, whether or not a number of times, by which the second biological information meets the second condition with respect to the measurement subject, exceeds a second value; select a third message when the second value is not exceeded; and select a fourth message when the second value is exceeded.

In an information processing apparatus according to a second mode of this invention, the first to fourth messages include different messages.

In an information processing apparatus according to a third mode of this invention, the first biological information includes an average value of blood pressure values in at least five days in one week, the blood pressure being measured at one or more opportunities in each of the five days, and the second biological information includes an average value of blood pressures measured at least at one opportunity in one week.

In an information processing apparatus according to a fourth mode of this invention, the determining as to whether or not to meet the first condition includes, at least, determining whether or not a systolic blood pressure value included in the first biological information is a third value or more, or whether or not a diastolic blood pressure value included in the first biological information is a fourth value or more, and the determining as to whether or not to meet the second condition includes, at least, determining whether or not a systolic blood pressure value included in the second biological information is a fifth value or more, or whether or not a diastolic blood pressure value included in the second biological information is a sixth value or more.

An information processing apparatus according to a fifth mode of this invention is configured to determine, when biological information of the measurement subject is received, whether the biological information is the first biological information or the second biological information.

An information processing apparatus according to a sixth mode of this invention is configured to: determine whether or not the first biological information meets a third condition; determine, when the first biological information meets the third condition, whether or not the first biological information meets the first condition; and selects a fifth message when the first biological information fails to meet the third condition.

An information processing apparatus according to a seventh mode of this invention is configured to cause a device, which supplies the first biological information or the second biological information, to display the selected message.

In an information processing apparatus according to an eighth mode of this invention, each of the first message and the second message includes at least a message which recommends a consultation to a medical institution, and each of the third message and the fourth message includes at least a message which recommends a consultation to a medical specialist, or a lifestyle-related disease certified physician.

In an information processing apparatus according to a ninth mode of this invention, the first period is a daytime period, and the second period is a nighttime period.

An information processing apparatus according to a tenth mode of this invention includes a storage unit configured to store the first biological information and the second biological information.

According to the present invention, there can be provided a technology which makes it possible to support a measurement subject in judging by himself/herself whether or not to consult a medical institution, a medical specialist, or a lifestyle-related disease certified physician.

BRIEF DESCRIPTION OF THE DRAWINGS

FIG. 1 is a block diagram schematically illustrating an example of an information processing system including an information processing apparatus according to an application example.

FIG. 2 is a block diagram illustrating an entire configuration of the information processing system including the information processing apparatus according to the first embodiment.

FIG. 7 is a block diagram schematically illustrating an example of a functional configuration of the server.

FIG. 12 is a flowchart illustrating an example of the processing procedure of the information processing apparatus according to the first embodiment.

FIG. 14 is a flowchart illustrating an example of a processing procedure of an information processing apparatus according to a third embodiment.

FIG. 17 is a flowchart illustrating an example of the processing procedure of the information processing apparatus according to the fourth embodiment.

FIG. 18 is a flowchart illustrating an example of a processing procedure of an information processing apparatus according to a fifth embodiment.

DETAILED DESCRIPTION

Figure 3:
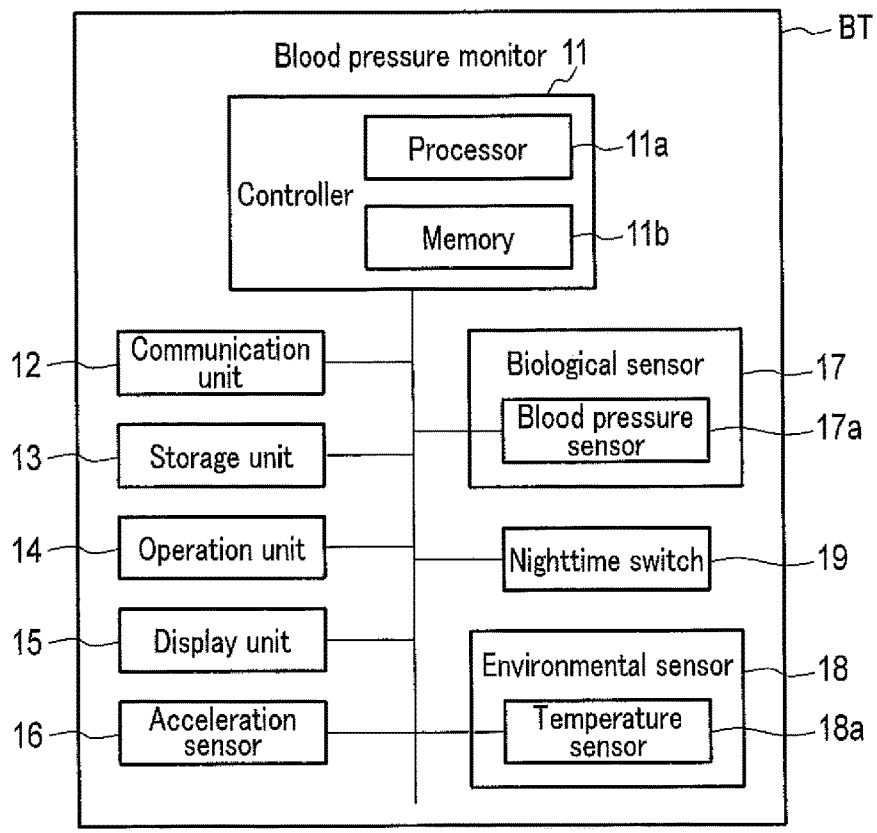
FIG. 3 is a block diagram illustrating a configuration example of a blood pressure monitor.

Hereinafter, an embodiment (also referred to as "present embodiment") according to one aspect of the present invention will be described with reference to the accompanying drawings. However, the present embodiment to be described below is merely an example of the present invention in all aspects. Needless to say, various improvements or modifications can be made without departing from the scope of the present invention. Specifically, when the present invention is implemented, concrete configurations corresponding to the embodiment may be adopted as appropriate. Note that although the data appearing in the present embodiment is described by a natural language, the data is, to be more specific, designated by a computer-recognizable pseudo-language, commands, parameters, machine languages, etc.

Application Example

To begin with, referring to FIG. 1, an example of a scene, in which the present invention is applied, will be described. FIG. 1 schematically illustrates an example of an information processing apparatus according to an application example.

Even if a measurement subject simply measures a blood pressure in the home or the like, the measurement subject cannot judge whether or not the measurement subject himself/herself should consult a medical institution, a medical specialist, or a lifestyle-related disease certified physician. Thus, in the application example, a description is given of an information processing apparatus which makes it possible to propose whether or not such a measurement subject should consult a medical institution, a medical specialist, or a lifestyle-related disease certified physician.

Configuration of Application Example

Before describing the configuration of the information processing apparatus, the outline of the information processing apparatus is described. The information processing apparatus proposes whether or not to consult a medical institution, a medical specialist, or a lifestyle-related disease certified physician, based on received biological information (including a blood pressure value) of a user (a measurement subject). Hereinafter, "blood pressure value" means a systolic blood pressure SYS and a diastolic blood pressure DIA. Note that the blood pressure value is simply described as "blood pressure value", unless the systolic blood pressure SYS and diastolic blood pressure DIA are not distinguished.

As illustrated in FIG. 1, an information processing apparatus IPE includes a reception unit IPER, an information storage unit IPEB, a determination unit IPED, a message storage unit IPEM, a message selection unit IPES, and a message transmission unit IPET.

The reception unit IPER receives biological information (including a blood pressure value) of a user (a measurement subject), an instruction, a response to a message, and the like, from an arbitrary terminal (e.g. a user terminal: a terminal which a user uses).

The information storage unit IPEB stores the received biological information on a user-by-user basis.

The determination unit IPED determines whether or not the biological information stored in the information storage unit IPEB satisfies a predetermined condition.

The message storage unit IPEM stores a plurality of messages which are transmitted to the user terminal.

The message selection unit IPES determines a message which is to be transmitted to the user terminal, based on a determination result of the determination unit IPED.

The message transmission unit IPET transmits (issues) the message, which is determined by the message selection unit IPES, to the user terminal.

Operation of the Application Example

Next, a description is given of an example of an operation (a consultation recommendation operation) in which the information processing apparatus IPE proposes whether or not to consult a medical institution, a medical specialist, or a lifestyle-related disease certified physician. At the time of the consultation recommendation operation, the information processing apparatus IPE performs, for example, either an operation relating biological information in the daytime, or an operation relating biological information in the nighttime.

Upon receiving an instruction to perform the consultation recommendation operation, the determination unit IPED determines whether the consultation recommendation operation is the operation relating to daytime biological information, or the operation relating nighttime biological information.

Here, a description is given of a case of determining that the information processing apparatus IPE performs the operation relating daytime biological information. To begin with, the determination unit IPED determines whether or not first biological information (an average value of blood pressure values in at least five days in one week, the blood pressure being measured at one or more opportunities in each of the five days (hereinafter, for the purpose of simplicity, also described as "an average value of blood pressures measured at five opportunities in one week")) of the user meets a first condition (an average value of the systolic blood pressure SYS exceeds 135 mmHg; or an average value of the diastolic blood pressure DIA exceeds 85 mmHg; or an average value of the systolic blood pressure SYS exceeds 135 mmHg and an average value of the diastolic blood pressure DIA exceeds 85 mmHg). Then, if the determination unit IPED determines that the first biological information meets the first condition, the determination unit IPED determines, with respect to the user, whether the number of times, by which the first biological information meets the first condition, exceeds a first value (e.g. "2"). When the number of times does not exceed the first value, the message selection unit IPES selects a first message (e.g. a message recommending a consultation to a medical institution). When the number of times exceed the first value, the message selection unit IPES selects a second message (e.g. a message different from the first message). Then, the message transmission unit IPET transmits the selected message, which is received from the message storage unit IPEM, to the user terminal. In this manner, the operation relating to the daytime biological information is performed. Note that one opportunity is the unit of an opportunity of measuring a blood pressure. For example, even if the blood pressure is successively measured twice in the morning, or is measured only once in the morning, the opportunity of blood pressure measurement is counted as one opportunity.

Next, a description is given of a case of determining that the information processing apparatus IPE performs the operation relating to nighttime biological information. To begin with, the determination unit IPED determines whether or not second biological information (for example, an average value of blood pressures measured at least at one opportunity in one week) of the user meets a second condition (an average value of the systolic blood pressure SYS exceeds 120 mmHg; or an average value of the diastolic blood pressure DIA exceeds 85 mmHg; or an average value of the systolic blood pressure SYS exceeds 120 mmHg and an average value of the diastolic blood pressure DIA exceeds 85 mmHg). Then, if the determination unit IPED determines that the second biological information meets the second condition, the determination unit IPED determines, with respect to the user, whether the number of times, by which the second biological information meets the second condition, exceeds a second value (e.g. "2"). When the number of times does not exceed the second value, the message selection unit IPES selects a third message (e.g. a message recommending a consultation to a medical specialist or a lifestyle-related disease certified physician. When the number of times exceed the second value, the message selection unit IPES selects a fourth message (e.g. a message different from the third message). Then, the message transmission unit IPET transmits the selected message, which is received from the message storage unit IPEM, to the user terminal. In this manner, the operation relating to the nighttime biological information is performed.

Note that the first condition and the second condition are determined, for example, based on the JSH Guidelines for the Management of Hypertension 2014.

Advantageous Effects of the Application Example

According to the JSH Guidelines for the Management of Hypertension 2014, the conditions for use in the judgment relating to hypertension in the daytime are different from the conditions for use in the judgment relating to hypertension in the nighttime. In addition, in some cases, it is preferable that the consultation recommendation message based on the measurement result in the daytime is different from the consultation recommendation message based on the measurement result in the nighttime.

The information processing apparatus IPE according to the application example performs, under the different conditions, the determination of hypertension in the operation relating to daytime biological information and the determination of hypertension in the operation relating to nighttime biological information, and transmits the different messages to the user terminal in the operation relating to daytime biological information and in the operation relating to nighttime biological information.

Thus, even when the user does not grasp the content of the JSH Guidelines for the Management of Hypertension 2014, if the user simply measures the blood pressure value, the information processing apparatus IPE can appropriately judge whether or not the user should consult a medical institution, a medical specialist, or a lifestyle-related disease certified physician.

<1> First Embodiment

Hereinafter, a first embodiment according to the above-described application example will be described.

<1-1> Configuration
<1-1-1> Information Processing System

FIG. 2 is a block diagram illustrating an entire configuration of an information processing system including an information processing apparatus according to a first embodiment. As illustrated in FIG. 2, the information processing system includes, for example, a plurality of user terminals UT (in FIG. 2, UT1 to UTn; n is an arbitrary integer), a communication network NW, a server SV, and a plurality of doctor terminals DT (in FIG. 2, DT1 to DTm; m is an arbitrary integer). The user terminals UT1 to UTn, server SV and doctor terminals DT1 to DTm are mutually communicable via the communication network NW. Note that when the user terminals UT1 to UTn are not distinguished from each other, the user terminal is simply referred to as "user terminal UT". Similarly, when the doctor terminals DT1 to DTm are not distinguished from each other, the doctor terminal is simply referred to as "doctor terminal DT". The user terminal UT is an example of the "user terminal" of the application example. The server SV is an example of the "information processing apparatus IPE" of the application example.

<1-1-1-1> User Terminal

As illustrated in FIG. 2, each of the user terminals UT1 to UTn includes a blood pressure monitor (blood pressure measuring unit), BT1 to BTn, and a portable information terminal, IT1 to ITn. Note that when the blood pressure monitors BT1 to BTn are not distinguished from each other, the blood pressure monitor is described simply as "blood pressure monitor BT". Similarly, when the portable information terminals IT1 to ITn are not distinguished from each other, the portable information terminal is described simply as "portable information terminal IT".

<1-1-1-1-1> Blood Pressure Monitor

Before describing a concrete configuration of the blood pressure monitor BT, the outline of the blood pressure monitor BT will be described. The blood pressure monitor BT is, for example, a wristwatch-type wearable terminal. The blood pressure monitor BT is worn on the wrist of the user (measurement subject), and measures the blood pressure value by the user's operation, or at a preset timing or at preset time intervals. In addition, the blood pressure monitor BT transmits biological information, in which, for example, the user's blood pressure value (including the systolic blood pressure SYS and diastolic blood pressure DIA), the measurement date/time, user information (e.g. user ID) and a first flag are correlated, to the portable information terminal IT by, for example, a wireless interface. The user ID is an identifier which is assigned to each user. The first flag will be described later. In addition, the blood pressure monitor BT is not limited to the type that is worn on the wrist. The blood pressure monitor BT may be such a type that a cuff is wound on the upper arm or the like, or may be a stationary type. Further, the blood pressure monitors BT1 to BTn may be blood pressure monitors of different types.

Referring to FIG. 3, an example of the concrete configuration of the blood pressure monitor BT will be described. FIG. 3 is a block diagram illustrating a configuration example of the blood pressure monitor BT.

As illustrated in FIG. 3, the blood pressure monitor BT includes a controller 11, a communication unit 12, a storage unit 13, an operation unit 14, a display unit 15, an acceleration sensor 16, a biological sensor 17, an environmental sensor 18, and a nighttime switch 19.

The controller 11 includes, for example, a processor 11a and a memory 11b. The processor 11a executes programs by using the memory 11b, and thereby the controller 11 realizes various operation controls and data processing. The processor 11a is, for example, a CPU (Central Processing Unit) or MPU (Micro Processing Unit), which includes an arithmetic circuit. The memory 11b includes, for example, a nonvolatile memory which stores programs which the processor 11a executes, and a volatile memory such as a RAM (Random Access Memory) which is used as a working memory. The controller 11 includes a clock (not shown), and can measure the present date/time. The processor 11a can control the respective components and can execute data processing, by executing the programs which the memory 11b or storage unit 13 stores. Specifically, the processor 11a executes operation controls of the respective components in accordance with an operation signal from the operation unit 14, and executes data processing on the biological information which the biological sensor 17 and environmental sensor 18 measure.

The communication unit 12 is a communication interface for communication with the portable information terminal IT. As a communication interface, use is made of, for example, an interface adopting a short-range wireless data communication standard such as Bluetooth (trademark). The communication unit 12 transmits data to the portable information terminal IT, and receives data from the portable information terminal IT. The communication by the communication unit 12 may be either wireless communication or wire communication.

The storage unit 13 stores data of a program for controlling the blood pressure monitor BT, setup data for setting various functions of the blood pressure monitor BT, and biological information measured by the acceleration sensor 16, biological sensor 17 and environmental sensor 18. Note that the storage unit 13 may be used as a working memory at a time when the program is executed.

The operation unit 14 is composed of, for example, operation devices such as a touch panel and operation buttons (operation keys), which are not illustrated. The operation unit 14 detects an operation by the user, and outputs an operation signal indicative of the operation content to the controller 11. Note that the operation unit 14 is not limited to the touch panel and operation buttons. The operation unit 14 may include, for example, a speech recognition unit which recognizes an operation instruction by the user's speech, a biometrics authentication unit which authenticates a biological part of the user, and an image recognition unit which recognizes the user's facial expression or gesture by images acquired by photographing the user's face or body.

The display unit 15 includes, for example, a display screen (e.g. an LCD (Liquid Crystal Display) or EL (Electroluminescence) display), and an indicator, and displays information in accordance with a control signal from the controller 11.

The acceleration sensor 16 detects an acceleration which the main body of the blood pressure monitor BT receives. For example, the acceleration sensor acquires acceleration data of three axes or six axes. The acceleration data can be used in order to estimate an activity amount (posture and/or movement) of the user who wears the blood pressure monitor BT. The controller 11 can correlate the acceleration data, which the acceleration sensor 16 measures, with measurement date/time based on date/time information, and can output the correlated data as biological information.

The biological sensor 17 measures the user's biological information. The biological sensor 17 includes, for example, a blood pressure sensor 17a. The blood pressure sensor 17a measures the blood pressure value of the user.

It is assumed that the biological information which the biological sensor 17 acquires, is, aside from the blood pressure value, a heart rate, pulse wave data, electrocardiographic data, heartbeat data and body temperature data. Sensors for measuring such biological information may be provided as the biological sensor 17.

The blood pressure sensor 17a is a blood pressure sensor of a successive measurement type or a nonsuccessive measurement type. The blood pressure sensor 17a is a blood pressure sensor which can measure the value of the blood pressure (e.g. a systolic blood pressure and a diastolic blood pressure). The blood pressure sensor 17a may include a blood pressure sensor of a Beat by Beat (BbB) method which measures a blood pressure value on a beat-by-beat basis, but the blood pressure sensor 17a is not limited to this.

For example, as the blood pressure sensor 17a, a blood pressure sensor, which uses an oscillometric method, pulse transmit time (PTT) method, tonometry method, optical method, radio wave method or ultrasonic method, is applicable. The oscillometric method is a method in which the upper arm is pressed by a cuff, and a blood pressure value is measured by the oscillation waveform in the cuff. The PTT method is a method of measuring a pulse transmit time, and estimating a blood pressure value from the measured pulse transmit time. The tonometry method is a method of putting a pressure sensor in direct contact with a biological part where an artery, such as a radial artery of the wrist, passes, and measuring a blood pressure value by using information which the pressure sensor detects. The optical method, radio wave method and ultrasonic method are methods of applying light, radio waves or ultrasonic waves to a blood vessel, and measuring a blood pressure value from the reflected waves.

The environmental sensor 18 includes a sensor which measures environmental information of the surrounding of the user, and acquires measured environmental data. In the configuration example illustrated in FIG. 3, the environmental sensor 18 includes, for example, an air temperature sensor 18a. However, the environmental sensor 18 may include, as well as the air temperature sensor, sensors which measure a temperature, humidity, sound, light, and the like. The environmental sensor 18 may include a sensor which measures environmental information (environmental data) that is assumed to have a direct or indirect relation to a fluctuation of the blood pressure value. Further, the controller 11 can correlate environmental data, which the environmental sensor 18 measures, with a measurement date/time which is set based on date/time information, and can output the correlated data as environmental data.

When the nighttime switch 19 is pressed by, for example, the user, the pressing is reported to the controller 11. The controller 11 automatically measures the blood pressure value after several hours (e.g. after four hours) from the pressing of the nighttime switch 19. The controller 11 sets a first flag for a blood pressure value which is measured after the pressing of the nighttime switch 19 (with the nighttime switch 19 acting as a trigger).

Here, the first flag is described. The first flag is information for determining whether the measured blood pressure value was measured in the nighttime or measured in the daytime. Specifically, when the measurement of the blood pressure value was performed in the nighttime, the "first flag" is set (for example, the data of the first flag is set at "1"). When the measurement of the blood pressure value was performed in the daytime, the "first flag" is not set (for example, the data of the first flag is set at "0").

The controller 11 changes the first flag, based on the measurement date/time of the blood pressure value, or based on the nighttime switch 19. Concretely, the controller 11 sets the "first flag", when the measurement date/time of the blood pressure value is in the nighttime (e.g. 2:00 AM to 3:59 AM), or when the blood pressure value is measured with the nighttime switch 19 acting as a trigger. On the other hand, the controller 11 does not set the "first flag" (the controller 11 sets the data of the first flag to "0"), when the measurement date/time of the blood pressure value is in the daytime (e.g. 4:00 AM to 1:59 AM). The definitions of "nighttime" and "daytime" are described in, for example, the JSH Guidelines for the Management of Hypertension 2014.

Specifically, the blood pressure value measured with the nighttime switch 19 acting as a trigger is treated as the blood pressure value measured in the nighttime.

Hereinafter, the nighttime is also described as "first period", and the daytime is also described as "second period".

<1-1-1-1-2> Portable Information Terminal

Before describing a concrete configuration of the portable information terminal IT, the outline of the portable information terminal IT will be described. The portable information terminal IT is a smart device (typically, a smartphone, a tablet terminal). The portable information terminal IT receives biological information which is sent from the blood pressure monitor BT, and transfers the biological information to the server SV via the communication network NW. For example, application software (program) for managing the biological information may be installed in the portable information terminal IT. Note that the portable information terminals IT1 to ITn may be different types of terminals. In the meantime, when the biological information, which is received from the blood pressure monitor BT, is not correlated with the user ID, the portable information terminal IT may correlate the biological information, which is received from the blood pressure monitor BT, with the user ID. The user ID may be stored in the storage unit 22 or a memory 21b.

Figure 4:
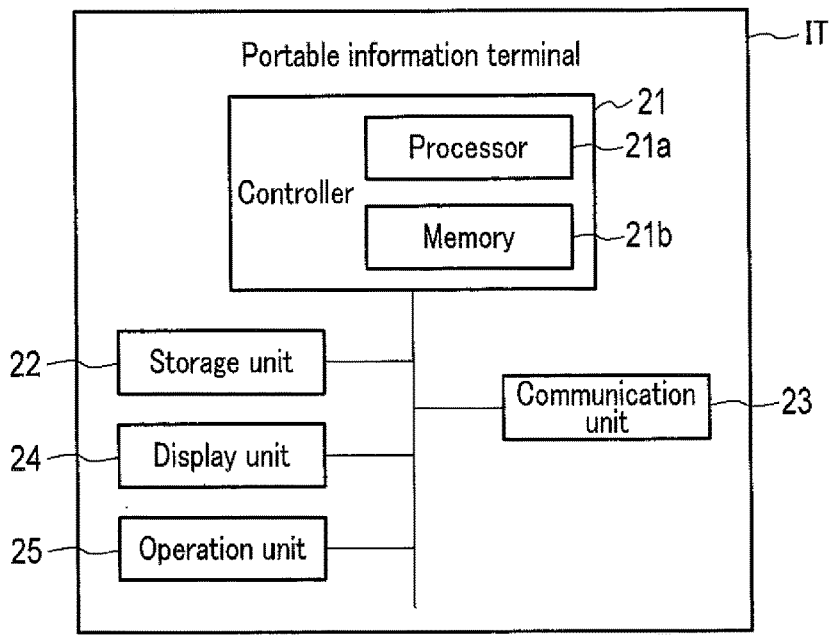
FIG. 4 is a block diagram illustrating a configuration example of a portable information terminal.

Referring to FIG. 4, an example of the concrete configuration of the portable information terminal IT will be described. FIG. 4 is a block diagram illustrating a configuration example of the portable information terminal IT.

As illustrated in FIG. 4, the portable information terminal IT includes a controller 21, a storage unit 22, a communication unit 23, a display unit 24, and an operation unit 25.

The controller 21 includes, for example, a processor 21a, and the memory 21b. Since the basic configuration of the controller 21 is the same as that of the controller 11, a detailed description thereof is omitted.

The storage unit 22 is composed of, for example, a semiconductor memory or a magnetic disk. The storage unit 22 may store programs which the processor 21a of the controller 21 executes. In addition, the storage unit 22 may store biological data which is supplied from the blood pressure monitor BT. Further, the storage unit 22 may also store display data which is displayed on the display unit 24.

The communication unit 23 is a communication interface for communicating with the blood pressure monitor BT and server SV. The communication unit 23 receives data from the blood pressure monitor BT, or transmits an operation instruction to the blood pressure monitor BT. The communication by the communication unit 23 may be either wireless communication or wire communication. Further, the communication unit 23 transmits data to the server SV via the network NW, or receives data from the server SV. The communication by the communication unit 23 may be either wireless communication or wire communication. In the present embodiment, the description is given on the assumption that the network NW is, for example, the Internet or the like. However, the network NW is not limited to this, and may be another kind of network such as a LAN, or the communication may be one-to-one communication using a communication cable such as a USB cable.

The display unit 24 includes a display screen (for example, an LCD, an EL display or the like). In the display unit 24, the display content, which is displayed on the display screen, is controlled by the control of the controller 21.

The operation unit 25 sends to the controller 21 an operation signal corresponding to an operation by the user. The operation unit 25 is, for example, a touch panel provided on the display screen of the display unit 24. The operation unit 25 is not limited to the touch panel, and may be an operation button, a keyboard, a mouse, and the like. In addition, the operation unit 25 may include a speech recognition unit which recognizes an operation instruction by the user's speech, a biometrics authentication unit which authenticates a biological part of the user, or an image recognition unit which recognizes the user's facial expression or gesture.

Note that when the blood pressure monitor BT is unable to transmit biological information to the portable information terminal IT, the portable information terminal IT may transmit to the server SV a blood pressure value which the user manually inputs.

<1-1-1-2> Doctor Terminal

Before describing a concrete configuration of the doctor terminal DT, the outline of the doctor terminal DT will be described. The doctor terminal DT is, for example, a stationary personal computer, a portable notebook-type personal computer, or a tablet terminal. The doctor terminal DT can transmit/receive data to/from the server SV, for example, by using a browser. Specifically, by using the browser, the doctor terminal DT can transmit information relating to the user to the server SV, and can display information which is transmitted from the server SV. Note that the doctor terminals DT1 to DTm may be different types of terminals. In addition, the doctor terminal DT may receive biological information from the blood pressure monitor BT, and may execute various processes.

Figure 5:
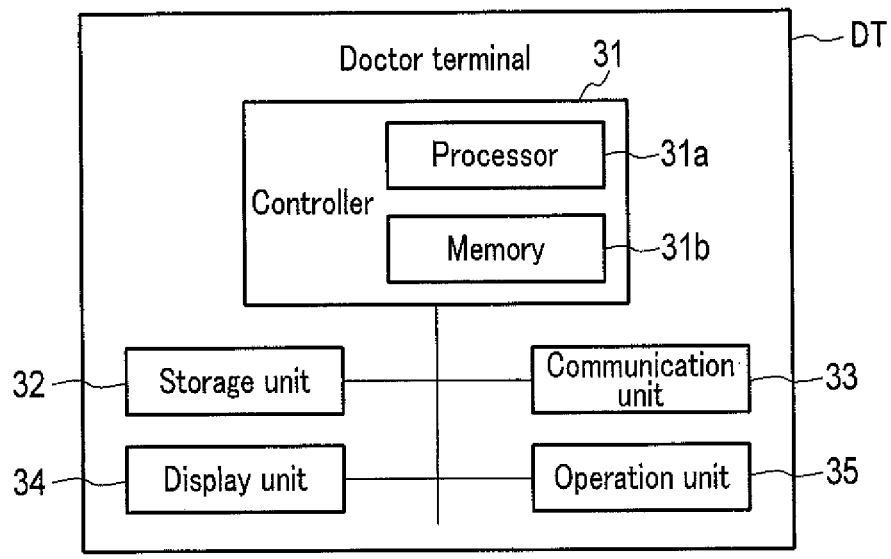
FIG. 5 is a block diagram illustrating a configuration example of a doctor terminal.

Referring to FIG. 5, an example of the concrete configuration of the doctor terminal DT will be described.

FIG. 5 is a block diagram illustrating a configuration example of the doctor terminal DT.

As illustrated in FIG. 5, the doctor terminal DT includes a controller 31, a storage unit 32, a communication unit 33, a display unit 34 and an operation unit 35.

The controller 31 includes, for example, a processor 31a and a memory 31b. Since the basic configuration of the controller 31 is the same as that of the controller 11, a detailed description thereof is omitted.

The storage unit 32 is composed of, for example, a magnetic disk, a semiconductor memory, an optical disc, a magneto-optical disc, or the like. The storage unit 32 may store programs which the processor 31a of the controller 31 executes.

The communication unit 33 is a communication interface for communicating with the server SV. The communication unit 33 transmits data to the server SV or receives data from the server SV via the network NW. The communication by the communication unit 33 may be either wireless communication or wire communication. In the present embodiment, the description is given on the assumption that the communication unit 33 communicates with the server SV via another kind of network such as a LAN. However, aside from this, the communication may include serial communication using a communication cable.

The display unit 34 includes a display screen (for example, an LCD, an EL display or the like). In the display unit 34, the display content, which is displayed on the display screen, is controlled by the control of the controller 31.

The operation unit 35 sends to the controller 31 an operation signal corresponding to an operation by the user. The operation unit 35 is, for example, a touch panel provided on the display screen of the display unit 34. The operation unit 35 is not limited to the touch panel, and may be an operation button, a keyboard, a mouse, and the like. In addition, the operation unit 35 may include a speech recognition unit which recognizes an operation instruction by the user's speech, a biometrics authentication unit which authenticates a biological part of the user, or an image recognition unit which recognizes the user's facial expression or gesture.

<1-1-1-3> Server

Before describing a concrete configuration of the server SV, the outline of the server SV will be described. The server SV is a server computer. In the present embodiment, the description is given on the assumption that a program (software) is installed in the server SV so as to cause a general-purpose computer apparatus to execute a process to be described later. The server SV accumulates biological information which is transmitted from the user terminal UT. The server SV may transmit the user's biological information in response to an access from the doctor terminal DT which a medical institution, a medical specialist or a lifestyle-related disease certified physician possesses, for example, so as to provide the biological information for the health guidance or diagnosis of the user. Note that an example of the function, which the server SV realizes, will be described later.

Figure 6:
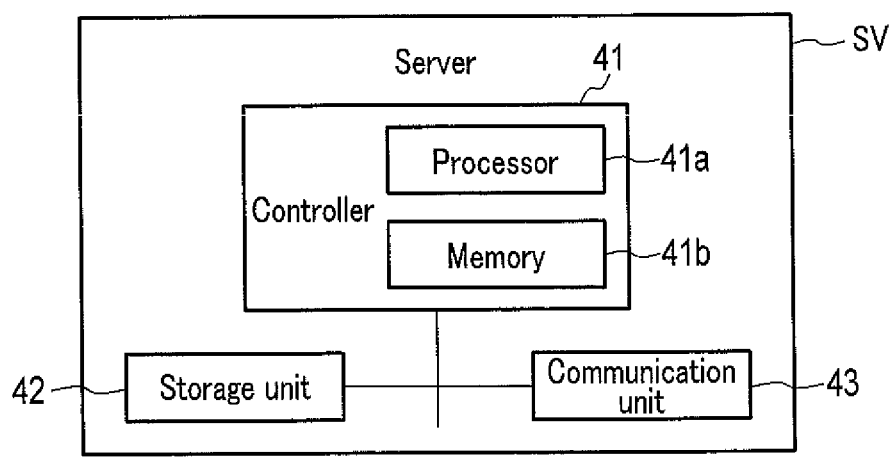
FIG. 6 is a block diagram illustrating a configuration example of a server.

Referring to FIG. 6, an example of the concrete configuration of the server SV will be described. FIG. 6 is a block diagram illustrating a configuration example of the server SV.

As illustrated in FIG. 6, the server SV includes a controller 41, a storage unit 42 and a communication unit 43.

The controller 41 includes, for example, a processor 41a and a memory 41b. Since the basic configuration of the controller 41 is the same as that of the controller 11, a detailed description thereof is omitted.

The storage unit 42 is composed of, for example, a magnetic disk, a semiconductor memory, an optical disc, a magneto-optical disc, or the like. The storage unit 42 stores various kinds of biological information acquired from the user terminal UT. In addition, the storage unit 42 may store programs which the processor 41a of the controller 41 executes.

The communication unit 43 is a communication interface for communicating with the user terminal UT or doctor terminal DT. The communication unit 43 transmits data to the user terminal UT or doctor terminal DT via the network NW, or receives data from the user terminal UT or doctor terminal DT via the network NW. The communication by the communication unit 43 may be either wireless communication or wire communication.

<1-1-2> Functional Configuration of the Server

Next, referring to FIG. 7, an example of the functional configuration of the server SV according to the present embodiment will be described. FIG. 7 is a block diagram schematically illustrating an example of the functional configuration of the server SV according to the present embodiment.

The controller 41 of the server SV loads a program, which is stored in the storage unit 42, into the memory 41b. Then, the controller 41 interprets and executes, by the processor 41a, the program loaded in the memory 41b, and controls the respective structural elements of the server SV. Thereby, as illustrated in FIG. 7, the server SV according to the present embodiment functions as a computer including a reception unit 51, a controller 52, an information storage unit 53, a condition determination unit 54, a message selection unit 55, a message storage unit 56, and a message transmission unit 57. The reception unit 51 is an example of the "reception IPER" of the application example. The information storage unit 53 is an example of the "information storage unit IPEB" of the application example. The condition determination unit 54 is an example of the "determination unit IPED" of the application example. The message selection unit 55 is an example of the "message selection unit IPES" of the application example. The message storage unit 56 is an example of the "message storage unit IPEM" of the application example. The message transmission unit 57 is an example of the "message transmission unit IPET" of the application example.

The reception unit 51 receives biological information, an instruction, or a response to a message (simply referred to as "response"), and supplies the biological information, instruction or response to the controller 52.

Based on the biological information, instruction or response from the reception unit 51, the controller 52 starts a consultation recommendation operation, or updates the biological information stored in the information storage unit 53.

Based on the response, the controller 52 adds flags (e.g. second to n-th (n is an arbitrary integer) flags) to the biological information.

Based on the instruction or response from the reception unit 51, the controller 52 starts the consultation recommendation operation, or updates the biological information stored in the information storage unit 53.

The information storage unit 53 includes data storage areas for respective users. By managing the data storage areas on a user-by-user basis, it is possible to appropriately manage biological management information including biological information of a plurality of measurement subjects. The data storage areas are developed, for example, in the memory 41b or storage unit 42 of the server SV. The data storage areas store, for example, biological information which is received via the network NW. An example of the data storage areas will be described later. The information storage unit 53 may be configured to be displayable on the portable information terminal IT or doctor terminal DT, for example, by the user's instruction via the portable information terminal IT or doctor terminal DT.

The condition determination unit 54 determines whether or not the biological information stored in the information storage unit 53 satisfies a predetermined condition. The condition determination unit 54 can determine whether the period in which biological information of a target was measured is a nighttime period or a daytime period, by referring to a "first flag".

The message selection unit 55 selects a message, based on a determination result supplied from the condition determination unit 54.

The message storage unit 56 stores a plurality of messages. The message storage unit 56 supplies a message, which is selected by the message selection unit 55, to the message transmission unit 57. The message storage unit 56 is developed, for example, in the memory 41b or storage unit 42 of the server SV. The messages stored in the message storage unit 56 can be changed as appropriate. The message storage unit 56 may be configured to be displayable on the portable information terminal IT or doctor terminal DT, for example, by the user's instruction via the portable information terminal IT or doctor terminal DT.

The message transmission unit 57 transmits (issues) the message, which is supplied from the message storage unit 56, to, for example, the portable information terminal IT or doctor terminal DT.

For example, the user can receive, by the portable information terminal IT, a message from the message transmission unit 57, and can confirm the message. In addition, there are some messages which request responses from the user. If the user makes a response to a message by the portable information terminal IT, the response is delivered to the reception unit 51.

<1-1-3> Configuration Example of the Data Storage Areas

Next, an example of the data storage areas of the information storage unit 53 will be described. For the purpose of simplicity, the data storage area is described, with attention being paid to one user.

The data storage area stores, for example, with respect to each user information (e.g. user ID) included in the biological information, a measurement date/time included in the biological information, a systolic blood pressure SYS included in the biological information, a diastolic blood pressure DIA included in the biological information, and a first flag, and second to n-th flags included in the biological information.

Note that the first flag is, as described above, a flag indicating whether the measurement date/time of the blood pressure value is "nighttime or daytime". In addition, the second to n-th flags are flags indicative of responses to messages. Besides, the data storage area may include data other than the above.

For example, the information storage unit 53 can output the blood pressure value and flag, based on the user ID or the like.

In the description below, for the purpose of simplicity, the above-described data that is stored in the data storage area is defined as "biological management information."

<1-2> Operation

<1-2-1> Biological Information Storage Operation

Figure 8:
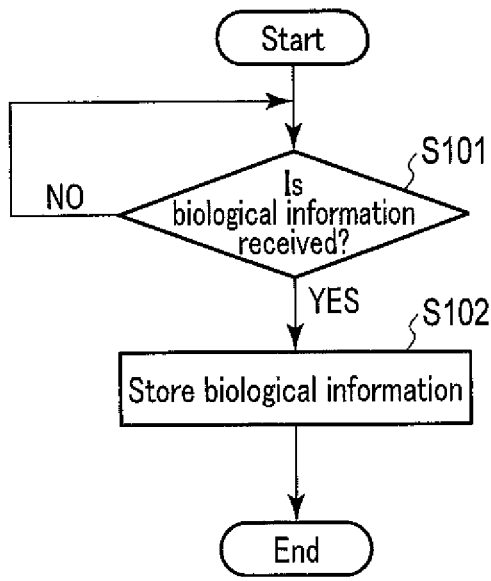
FIG. 8 is a flowchart illustrating an example of a processing procedure of the information processing apparatus according to the first embodiment.

Next, referring to FIG. 8, a description will be given of an example of a biological information storage operation of the information processing apparatus according to the first embodiment. FIG. 8 is a flowchart illustrating an example of a processing procedure of the information processing apparatus. Note that processing procedures to be described below are merely examples, and each process may be changed as much as possible. Further, in the processing procedures to be described below, omission, replacement and addition of steps can be made as appropriate in accordance with embodiments.

Here, a description is given of an operation of storing biological information in the information storage unit 53.

[Step S101]

The reception unit 51 stands by until receiving biological information via the network NW.

[Step S102]

When the reception unit 51 receives biological information, the biological information is stored in the information storage unit 53.

<1-2-2> Biological Management Information Update Operation

Figure 9:
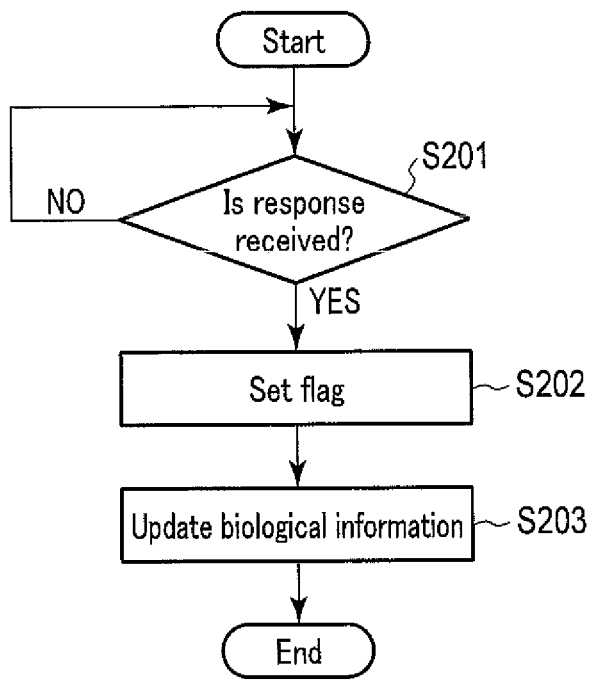
FIG. 9 is a flowchart illustrating an example of the processing procedure of the information processing apparatus according to the first embodiment.

Next, referring to FIG. 9, a description is given of an example of a biological management information update operation of the information processing apparatus according to the first embodiment. FIG. 9 is a flowchart illustrating an example of the processing procedure of the information processing apparatus. Note that processing procedures to be described below are merely examples, and each process may be changed as much as possible. Further, in the processing procedures to be described below, omission, replacement and addition of steps can be made as appropriate in accordance with embodiments.

Here, an operation of updating the biological management information stored in the information storage unit 53 will be described.

[Step S201]

The reception unit 51 stands by until receiving a response to a message.

[Step S202]

When the reception unit 51 receives a response to a message (step S201, Yes), the controller 52 specifies a user relating to the response. If the controller 52 specifies the user relating to the response, the controller 52 sets second to n-th flags as appropriate, according to the content of the response.

[Step S203]

After setting the second to n-th flags, the controller 52 updates the user's biological management information stored in the information storage unit 53.

<1-2-3> Consultation Recommendation Operation

Figure 10:
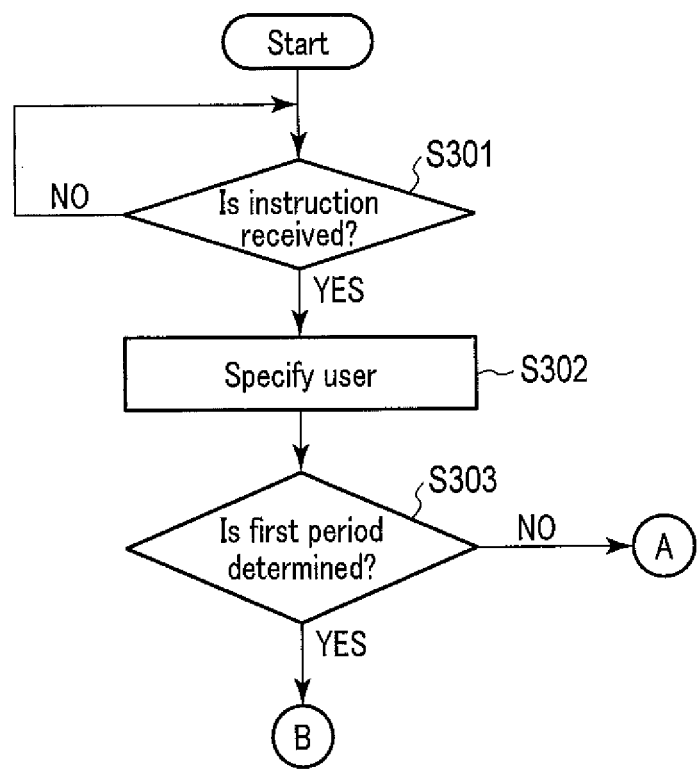
FIG. 10 is a flowchart illustrating an example of the processing procedure of the information processing apparatus according to the first embodiment.
Figure 11:
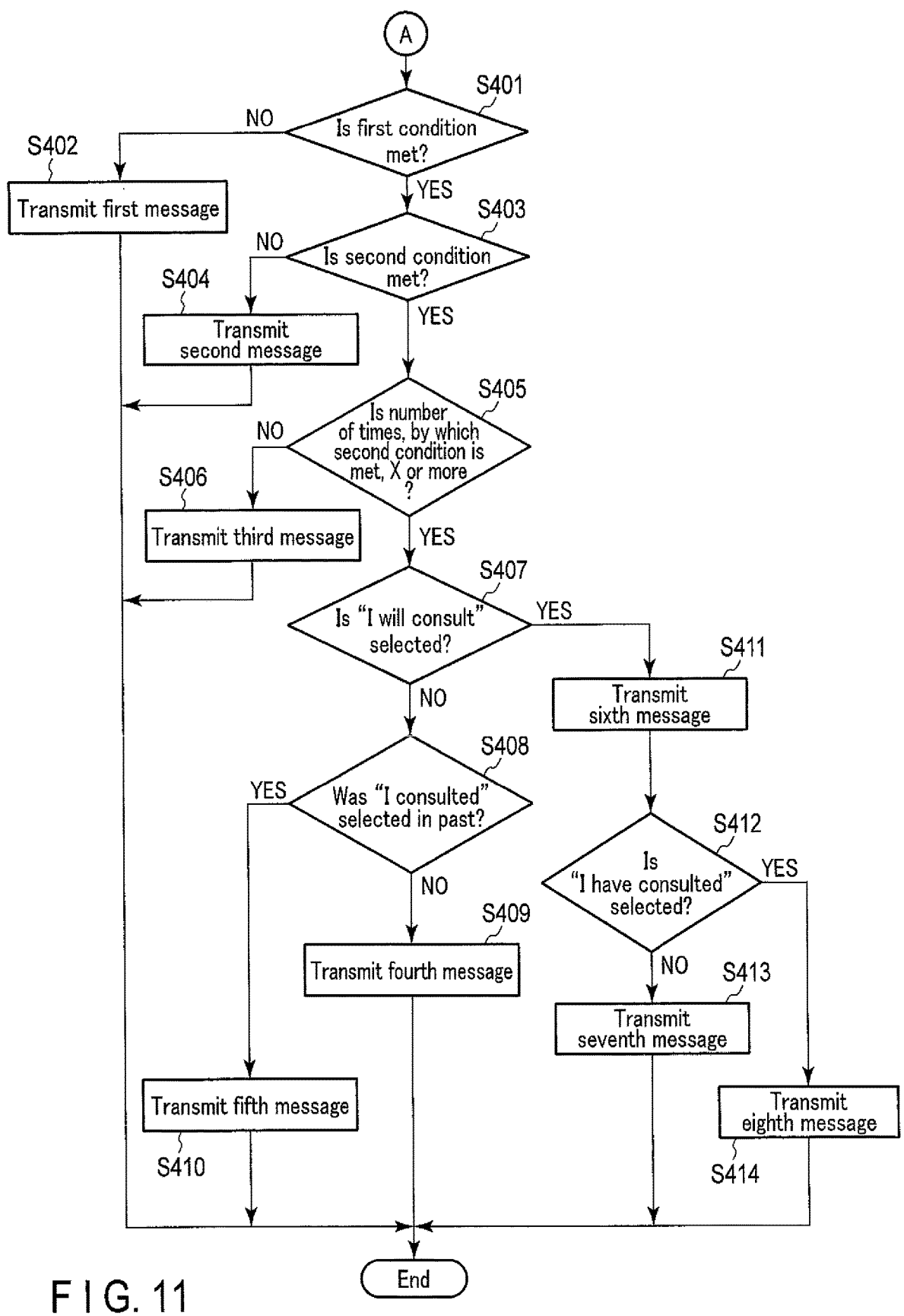
FIG. 11 is a flowchart illustrating an example of the processing procedure of the information processing apparatus according to the first embodiment.

Next, referring to FIG. 10 to FIG. 12, a description is given of an example of a consultation recommendation operation of the information processing apparatus according to the first embodiment. FIG. 10 to FIG. 12 are flowcharts illustrating an example of the processing procedure of the information processing system. Note that processing procedures to be described below are merely examples, and each process may be changed as much as possible. Further, in the processing procedures to be described below, omission, replacement and addition of steps can be made as appropriate in accordance with embodiments.

Here, a description is given of an operation in which the server SV performs consultation recommendation.

To begin with, referring to FIG. 10, a description is given of an initial operation of the consultation recommendation operation of the information processing apparatus according to the first embodiment.

[Step S301]

The reception unit 51 stands by until receiving an instruction to perform the consultation recommendation operation. Here, the instruction may be, for example, an instruction from the portable information terminal IT, or an instruction from the doctor terminal DT. It is also conceivable that the server SV automatically performs the consultation recommendation operation, responding to the reception of biological information. In this case, the reception of biological information may become an instruction.

[Step S302]

When the reception unit 51 receives an instruction to perform the consultation recommendation operation (step S301, YES), the controller 52 specifies a user of the target of the consultation recommendation operation.

[Step S303]

When the controller 52 specifies the user of the target of the consultation recommendation operation, the controller 52 determines whether or not the consultation recommendation operation is a consultation recommendation operation relating to a first period (nighttime). Specifically, the controller 52 determines which of a consultation recommendation operation relating to the first period and a consultation recommendation operation relating to a second period (daytime) is requested.

Referring to FIG. 11, a consultation recommendation operation following "A" in FIG. 10, i.e. a consultation recommendation operation relating to the second period, will be described. Here, the consultation recommendation operation relating to the second period is, for example, a consultation recommendation operation based on a blood pressure value measured in the daytime.

[Step S401]

If the controller 52 determines the consultation recommendation operation relating to the second period (step S303, NO), the condition determination unit 54 determines whether or not the information relating to the second period, which is stored in the information storage unit 53, meets a first condition.

The first condition is a condition relating to a daytime blood pressure value, which is described, for example, in the JSH Guidelines for the Management of Hypertension 2014. Specifically, the condition determination unit 54 determines whether or not blood pressure values in the daytime (4:00 AM to 1:59 AM) were measured at five opportunities in one week.

The first condition is stored, for example, in the memory 41b or storage unit 42 in the server SV. In addition, the first condition can be changed as appropriate.

[Step S402]

If the condition determination unit 54 refers to the biological management information stored in the information storage unit 53 and determines that the biological management information fails to meet the first condition (step S401, NO), the condition determination unit 54 reports this to the message selection unit 55.

The message selection unit 55 selects a first message which is to be displayed to the user, when the first condition is not met. The first message is, for example, a message to the effect that "Since the first condition is not met, the consultation recommendation operation cannot be executed." In addition, the first message may include a message to the effect that "If the blood pressure value is measured L times more in a predetermined period, the consultation recommendation operation can be executed." This first message can be changed as appropriate.

The message transmission unit 57 receives from the message storage unit 56 the first message which is selected by the message selection unit 55. Then, the message transmission unit 57 transmits the first message to the user (e.g. portable information terminal IT).

Thereby, the user can confirm the first message by a freely selected terminal. For example, by viewing the first message, the user can understand that the number of times of measurement is deficient in order to execute the consultation recommendation operation. Thus, the user can properly perform the measurement of the blood pressure value in order to execute the consultation recommendation operation.

[Step S403]

If the condition determination unit 54 refers to the biological management information stored in the information storage unit 53 and determines that the biological management information meets the first condition (step S401, YES), the condition determination unit 54 determines whether or not the biological management information stored in the information storage unit 53 meets a second condition.

The second condition is, for example, a condition relating to the determination of hypertension based on a daytime blood pressure value, which is described in the JSH Guidelines for the Management of Hypertension 2014. Specifically, the condition determination unit 54 determines whether or not an average value of the systolic blood pressure SYS in the daytime (4:00 AM to 1:59 AM), which were measured at five opportunities in one week, exceeds 135 mmHg; an average value of the diastolic blood pressure DIA measured at five opportunities in one week exceeds 85 mmHg; or an average value of the systolic blood pressure SYS exceeds 135 mmHg and an average value of the diastolic blood pressure DIA exceeds 85 mmHg.

The second condition is stored, for example, in the memory 41b or storage unit 42 in the server SV. In addition, the second condition can be changed as appropriate.

[Step S404]

If the condition determination unit 54 refers to the biological management information stored in the information storage unit 53 and determines that the biological management information fails to meet the second condition (step S403, NO), the condition determination unit 54 reports this to the message selection unit 55.

The message selection unit 55 selects a second message which is to be displayed to the user, when the second condition is not met. The second message is, for example, a message to the effect that "Since the second condition is not met, hypertension is not detected and a consultation to a medical institution is unnecessary." This second message can be changed as appropriate.

The message transmission unit 57 receives from the message storage unit 56 the second message which is selected by the message selection unit 55. Then, the message transmission unit 57 transmits the second message to the user (e.g. portable information terminal IT).

Thereby, the user can confirm the second message by a freely selected terminal. For example, by viewing the second message, the user can understand that the user himself/herself is in good health.

[Step S405]

If the condition determination unit 54 refers to the biological management information stored in the information storage unit 53 and determines that the biological management information meets the second condition (step S403, YES), the condition determination unit 54 determines whether the number of times, by which the biological management information meets the second condition, is X or more (X is an integer). Here, for example, X is 2.

[Step S406]

If the condition determination unit 54 determines whether the number of times, by which the second condition is met, is not X or more (step S405, NO), the condition determination unit 54 reports this to the message selection unit 55.

The message selection unit 55 selects a third message which is to be displayed to the user, when the number of times, by which the second condition is met, is not X or more. The third message is, for example, a consultation recommendation message. Specifically, the third message is a message to the effect that "Will you consult a medical institution?". In addition, the third message includes a message to the effect that "A consultation to a medical institution is recommended." The third message can be changed as appropriate.

The message transmission unit 57 receives from the message storage unit 56 the third message which is selected by the message selection unit 55. Then, the message transmission unit 57 transmits the third message to the user (e.g. portable information terminal IT).

Thereby, the user can confirm the third message by a freely selected terminal. For example, by viewing the third message, the user can understand that the user himself/herself should consult a medical institution. Further, if the user makes a response (e.g. selection of "I will consult." or "I will not consult.") to the third message (the message to the effect that "Will you consult a medical institution?") by a freely selected terminal, the content of the response is reflected in the biological management information in the flow described in FIG. 9.

[Step S407]

If the condition determination unit 54 determines whether the number of times, by which the second condition is met, is X or more (step S405, YES), the condition determination unit 54 determines whether or not a response "I will consult a medical institution." is selected as the response to the previous consultation recommendation operation.

The condition determination unit 54 can perform this determination by referring to the biological management information stored in the information storage unit 53.

[Step S408]

If the condition determination unit 54 determines that the response "I will consult a medical institution." is not selected as the response to the previous consultation recommendation operation (step S407, NO), the condition determination unit 54 determines whether or not a response "I consulted a medical institution." was selected in the past.

The condition determination unit 54 can perform this determination by referring to the biological management information stored in the information storage unit 53.

[Step S409]

If the condition determination unit 54 determines that the response "I consulted a medical institution." was not selected in the past (step S408, NO), the condition determination unit 54 reports this to the message selection unit 55.

The message selection unit 55 selects a fourth message which is to be displayed to the user, when the response "I consulted a medical institution." was not selected in the past. The fourth message is, for example, a consultation recommendation message. For example, the fourth message is a message to the effect that "Will you consult a medical institution?". In addition, when it is determined that the user has hypertension for T consecutive weeks (T is an integer), the fourth message includes a message to the effect that "The cutoff value of hypertension is exceeded for T consecutive weeks. A consultation to a medical institution is recommended". The fourth message can be changed as appropriate.

The message transmission unit 57 receives from the message storage unit 56 the fourth message which is selected by the message selection unit 55. Then, the message transmission unit 57 transmits the fourth message to the user (e.g. portable information terminal IT).

Thereby, the user can confirm the fourth message by a freely selected terminal. For example, by viewing the fourth message, the user can understand that the user himself/herself should consult a medical institution. Further, if the user makes a response (e.g. selection of "I will consult." or "I will not consult.") to the fourth message (the message to the effect that "Will you consult a medical institution?") by a freely selected terminal, the content of the response is reflected in the biological management information in the flow described in FIG. 9.

[Step S410]

If the condition determination unit 54 determines that the response "I consulted a medical institution" was selected in the past (step S408, YES), the condition determination unit 54 reports this to the message selection unit 55.

The message selection unit 55 selects a fifth message which is to be displayed to the user, when the response "I consulted a medical institution" was selected in the past. For example, the fifth message is a message to the effect that "Carry on with medical treatment according to the doctor's instructions." The fifth message can be changed as appropriate.

The message transmission unit 57 receives from the message storage unit 56 the fifth message which is selected by the message selection unit 55. Then, the message transmission unit 57 transmits the fifth message to the user (e.g. portable information terminal IT).

Thereby, the user can confirm the fifth message by a freely selected terminal. For example, by viewing the fifth message, the user can keep the motivation for his/her own medical treatment.

[Step S411]

If the condition determination unit 54 determines that the response "I will consult a medical institution." is selected as the response to the previous consultation recommendation operation (step S407, YES), the condition determination unit 54 reports this to the message selection unit 55.

The message selection unit 55 selects a sixth message which is to be displayed to the user, when the response "I will consult a medical institution." is selected. For example, the sixth message is a message to the effect that "Have you consulted a medical institution?". The sixth message can be changed as appropriate.

The message transmission unit 57 receives from the message storage unit 56 the sixth message which is selected by the message selection unit 55. Then, the message transmission unit 57 transmits the sixth message to the user (e.g. portable information terminal IT).

Thereby, the user can confirm the sixth message by a freely selected terminal. If the user makes a response (e.g. selection of "I have consulted." or "I have not yet consulted.") to the sixth message (the message to the effect that "Have you consulted a medical institution?") by a freely selected terminal, the content of the response is reflected in the biological management information in the flow described in FIG. 9.

[Step S412]

The condition determination unit 54 determines whether or not the response "I have consulted a medical institution." is selected as a response result of the sixth message.

[Step S413]

If the condition determination unit 54 determines that the response "I have consulted a medical institution" is not selected as the response result of the sixth message (step S412, NO), the condition determination unit 54 reports this to the message selection unit 55.

The message selection unit 55 selects a seventh message which is to be displayed to the user, when the response "I have consulted a medical institution" is not made. The seventh message is, for example, a consultation recommendation message. The seventh message is a message to the effect that "A consultation to a medical institution is recommended." In addition, the seventh message includes a message "Will you consult a medical institution?". The seventh message can be changed as appropriate.

The message transmission unit 57 receives from the message storage unit 56 the seventh message which is selected by the message selection unit 55. Then, the message transmission unit 57 transmits the seventh message to the user (e.g. portable information terminal IT).

Thereby, the user can confirm the seventh message by a freely selected terminal. For example, by viewing the seventh message, the user can understand that the user himself/ herself should consult a medical institution. Further, if the user makes a response (e.g. selection of "I will consult." or "I will not consult.") to the seventh message (the message to the effect that "Will you consult a medical institution?") by a freely selected terminal, the content of the response is reflected in the biological management information in the flow described in FIG. 9.

[Step S414]

If the condition determination unit 54 determines that the response "I have consulted a medical institution" is selected as the response result of the sixth message (step S412, YES), the condition determination unit 54 reports this to the message selection unit 55.

The message selection unit 55 selects an eighth message which is to be displayed to the user, when the response "I consulted a medical institution" was selected in the past. For example, the eighth message is a message to the effect that "Carry on with medical treatment according to the doctor's instructions." The eighth message can be changed as appropriate.

The message transmission unit 57 receives from the message storage unit 56 the eighth message which is selected by the message selection unit 55. Then, the message transmission unit 57 transmits the eighth message to the user (e.g. portable information terminal IT).

Thereby, the user can confirm the eighth message by a freely selected terminal. For example, by viewing the eighth message, the user can keep the motivation for his/her own medical treatment.

Referring to FIG. 12, a consultation recommendation operation following "B" in FIG. 10, i.e. a consultation recommendation operation relating to the first period, will be described. Here, the consultation recommendation operation relating to the first period is, for example, a consultation recommendation operation based on a blood pressure value measured in the nighttime.

[Step S501]

If the controller 52 determines the consultation recommendation operation relating to the first period (step S303, YES), the condition determination unit 54 determines whether or not the information relating to the first period, which is stored in the information storage unit 53, meets a third condition.

The third condition is, for example, a condition relating to the determination of hypertension based on a nighttime blood pressure value, which is described in the JSH Guidelines for the Management of Hypertension 2014. Specifically, the condition determination unit 54 determines whether or not an average value of the systolic blood pressure SYS in the nighttime (2:00 AM to 3:59 AM), which was measured at least at one opportunity in one week, exceeds 120 mmHg; an average value of the diastolic blood pressure DIA in the nighttime, which was measured at least at one opportunity in one week, exceeds 85 mmHg; or an average value of the systolic blood pressure SYS exceeds 120 mmHg and an average value of the diastolic blood pressure DIA exceeds 85 mmHg.

The third condition is stored, for example, in the memory 41b or storage unit 42 in the server SV. In addition, the third condition can be changed as appropriate.

[Step S502]

If the condition determination unit 54 refers to the biological management information stored in the information storage unit 53 and determines that the biological management information fails to meet the third condition (step S501, NO), the condition determination unit 54 reports this to the message selection unit 55.

The message selection unit 55 selects a ninth message which is to be displayed to the user, when the third condition is not met. The ninth message is, for example, a message to the effect that "Since the third condition is not met, hypertension is not detected and a consultation to a medical institution is unnecessary." This ninth message can be changed as appropriate.

The message transmission unit 57 receives from the message storage unit 56 the ninth message which is selected by the message selection unit 55. Then, the message transmission unit 57 transmits the ninth message to the user (e.g. portable information terminal IT).

Thereby, the user can confirm the ninth message by a freely selected terminal. For example, by viewing the ninth message, the user can understand that the user himself/herself is in good health.

[Step S503]

If the condition determination unit 54 refers to the biological management information stored in the information storage unit 53 and determines that the biological management information meets the third condition (step S501, YES), the condition determination unit 54 determines whether the number of times, by which the biological management information meets the third condition, is Y or more (Y is an integer). Here, for example, Y is 2.

[Step S504]

If the condition determination unit 54 determines whether the number of times, by which the third condition is met, is not Y or more (step S503, NO), the condition determination unit 54 reports this to the message selection unit 55.

The message selection unit 55 selects a tenth message which is to be displayed to the user, when the number of times, by which the third condition is met, is not Y or more. The tenth message is, for example, a consultation recommendation message. Specifically, the tenth message is a message to the effect that "Will you consult a medical specialist or a lifestyle-related disease certified physician?". In addition, the tenth message includes a message to the effect that "A consultation to a medical specialist or a lifestyle-related disease certified physician is recommended." The tenth message can be changed as appropriate.

The message transmission unit 57 receives from the message storage unit 56 the tenth message which is selected by the message selection unit 55. Then, the message transmission unit 57 transmits the tenth message to the user (e.g. portable information terminal IT).

Thereby, the user can confirm the tenth message by a freely selected terminal. For example, by viewing the tenth message, the user can understand that the user himself/herself should consult a medical specialist or a lifestyle-related disease certified physician. Further, if the user makes a response (e.g. selection of "I will consult." or "I will not consult.") to the tenth message (the message to the effect that "Will you consult a medical specialist or a lifestyle-related disease certified physician?") by a freely selected terminal, the content of the response is reflected in the biological management information in the flow described in FIG. 9.

[Step S505]

If the condition determination unit 54 determines whether the number of times, by which the third condition is met, is Y or more (step S503, YES), the condition determination unit 54 determines whether or not a response "I will consult a medical specialist or a lifestyle-related disease certified physician." is selected as the response to the previous consultation recommendation operation.

The condition determination unit 54 can perform this determination by referring to the biological management information stored in the information storage unit 53.

[Step S506]

If the condition determination unit 54 determines that the response "I will consult a medical specialist or a lifestyle-related disease certified physician." is not selected as the response to the previous consultation recommendation operation (step S505, NO), the condition determination unit 54 determines whether or not a response "I consulted a medical specialist or a lifestyle-related disease certified physician." was selected in the past.

The condition determination unit 54 can perform this determination by referring to the biological management information stored in the information storage unit 53.

[Step S507]

If the condition determination unit 54 determines that the response "I consulted a medical specialist or a lifestyle-related disease certified physician." was not selected in the past (step S506, NO), the condition determination unit 54 reports this to the message selection unit 55.

The message selection unit 55 selects an eleventh message which is to be displayed to the user, when the response "I consulted a medical specialist or a lifestyle-related disease certified physician." was not selected in the past. The eleventh message is, for example, a consultation recommendation message. For example, the eleventh message is a message to the effect that "Will you consult a medical specialist or a lifestyle-related disease certified physician?". In addition, when it is determined that the user has hypertension for T consecutive weeks (T is an integer), the eleventh message includes a message to the effect that "The cutoff value of hypertension is exceeded for T consecutive weeks. A consultation to a medical specialist or a lifestyle-related disease certified physician is recommended". The eleventh message can be changed as appropriate.

The message transmission unit 57 receives from the message storage unit 56 the eleventh message which is selected by the message selection unit 55. Then, the message transmission unit 57 transmits the eleventh message to the user (e.g. portable information terminal IT).

Thereby, the user can confirm the eleventh message by a freely selected terminal. For example, by viewing the eleventh message, the user can understand that the user himself/herself should consult a medical specialist or a lifestyle-related disease certified physician. Further, if the user makes a response (e.g. selection of "I will consult." or "I will not consult.") to the eleventh message (the message to the effect that "Will you consult a medical specialist or a lifestyle-related disease certified physician?") by a freely selected terminal, the content of the response is reflected in the biological management information in the flow described in FIG. 9.

[Step S508]

If the condition determination unit 54 determines that the response "I consulted a medical specialist or a lifestyle-related disease certified physician" was selected in the past (step S506, YES), the condition determination unit 54 reports this to the message selection unit 55.

The message selection unit 55 selects a twelfth message which is to be displayed to the user, when the response "I consulted a medical specialist or a lifestyle-related disease certified physician" was selected in the past. For example, the twelfth message is a message to the effect that "Carry on with medical treatment according to the instructions of a medical specialist or a lifestyle-related disease certified physician." The twelfth message can be changed as appropriate.

The message transmission unit 57 receives from the message storage unit 56 the twelfth message which is selected by the message selection unit 55. Then, the message transmission unit 57 transmits the twelfth message to the user (e.g. portable information terminal IT).

Thereby, the user can confirm the twelfth message by a freely selected terminal. For example, by viewing the twelfth message, the user can keep the motivation for his/her own medical treatment.

[Step S509]

If the condition determination unit 54 determines that the response "I will consult a medical specialist or a lifestyle-related disease certified physician." is selected as the response to the previous consultation recommendation operation (step S505, YES), the condition determination unit 54 reports this to the message selection unit 55.

The message selection unit 55 selects a 13th message which is to be displayed to the user, when the response "I will consult a medical specialist or a lifestyle-related disease certified physician." is selected. For example, the 13th message is a message to the effect that "Have you consulted a medical specialist or a lifestyle-related disease certified physician?". The 13th message can be changed as appropriate.

The message transmission unit 57 receives from the message storage unit 56 the 13th message which is selected by the message selection unit 55. Then, the message transmission unit 57 transmits the 13th message to the user (e.g. portable information terminal IT).

Thereby, the user can confirm the 13th message by a freely selected terminal. If the user makes a response (e.g. selection of "I have consulted." or "I have not yet consulted.") to the 13th message (the message to the effect that "Have you consulted a medical specialist or a lifestyle-related disease certified physician?") by a freely selected terminal, the content of the response is reflected in the biological management information in the flow described in FIG. 9.

[Step S510]

The condition determination unit 54 determines whether the response "I have consulted a medical specialist or a lifestyle-related disease certified physician." is selected as a response result of the 13th message.

[Step S511]

If the condition determination unit 54 determines that the response "I have consulted a medical specialist or a lifestyle-related disease certified physician" is not selected as the response result of the sixth message (step S510, NO), the condition determination unit 54 reports this to the message selection unit 55.

The message selection unit 55 selects a 14th message which is to be displayed to the user, when the response "I have consulted a medical specialist or a lifestyle-related disease certified physician" is not made. The 14th message is, for example, a consultation recommendation message. The 14th message is a message to the effect that "A consultation to a medical specialist or a lifestyle-related disease certified physician is recommended." In addition, the 14th message includes a message "Will you consult a medical specialist or a lifestyle-related disease certified physician?". The 14th message can be changed as appropriate.

The message transmission unit 57 receives from the message storage unit 56 the 14th message which is selected by the message selection unit 55. Then, the message transmission unit 57 transmits the 14th message to the user (e.g. portable information terminal IT).

Thereby, the user can confirm the 14th message by a freely selected terminal. For example, by viewing the 14th message, the user can understand that the user himself/herself should consult a medical specialist or a lifestyle-related disease certified physician. Further, if the user makes a response (e.g. selection of "I will consult." or "I will not consult.") to the 14th message (the message to the effect that "Will you consult a medical specialist or a lifestyle-related disease certified physician?") by a freely selected terminal, the content of the response is reflected in the biological management information in the flow described in FIG. 9.

[Step S512]

If the condition determination unit 54 determines that the response "I have consulted a medical specialist or a lifestyle-related disease certified physician" is selected as the response result of the 13th message (step S510, YES), the condition determination unit 54 reports this to the message selection unit 55.

The message selection unit 55 selects a 15th message which is to be displayed to the user, when the response "I consulted a medical specialist or a lifestyle-related disease certified physician" was selected in the past. For example, the 15th message is a message to the effect that "Carry on with medical treatment according to the instructions of a medical specialist or a lifestyle-related disease certified physician." The 15th message can be changed as appropriate.

The message transmission unit 57 receives from the message storage unit 56 the 15th message which is selected by the message selection unit 55. Then, the message transmission unit 57 transmits the 15th message to the user (e.g. portable information terminal IT).

Thereby, the user can confirm the 15th message by a freely selected terminal. For example, by viewing the 15th message, the user can keep the motivation for his/her own medical treatment.

<1-3> Advantageous Effects

According to the above-described embodiment, the information processing apparatus determines whether or not the user should consult a medical institution, based on the daytime biological information. In addition, the information processing apparatus determines whether or not the user should consult a medical specialist or a lifestyle-related disease certified physician, based on the nighttime biological information. In the information processing apparatus, the conditions (e.g. the above-described first and second conditions) used in the consultation recommendation operation relating to the daytime biological information are different from the condition (e.g. the above-described third condition) used in the consultation recommendation operation relating to the nighttime biological information. Besides, the information processing apparatus transmits different messages to the user (e.g. portable information terminal IT), based on respective determination results.

As described above, even in the case of a user who does not grasp the guidelines, the user can easily judge whether or not to consult a medical institution, a medical specialist or a lifestyle-related disease certified physician, by measuring the blood pressure value by himself/herself. In this manner, according to the information processing apparatus of the above-described embodiment, it becomes possible to properly propose whether or not to consult a medical institution, a medical specialist or a lifestyle-related disease certified physician, based on the user's biological information.

<2> Second Embodiment

A second embodiment will be described. In the second embodiment, a description is given of another example of the consultation recommendation operation relating to the second period. The basic configuration and basic operation of an information processing apparatus according to the second embodiment are the same as those of the information processing apparatus according to the above-described first embodiment. Accordingly, a description of the matters described in the first embodiment is omitted.

<2-1> Consultation Recommendation Operation

Figure 13:
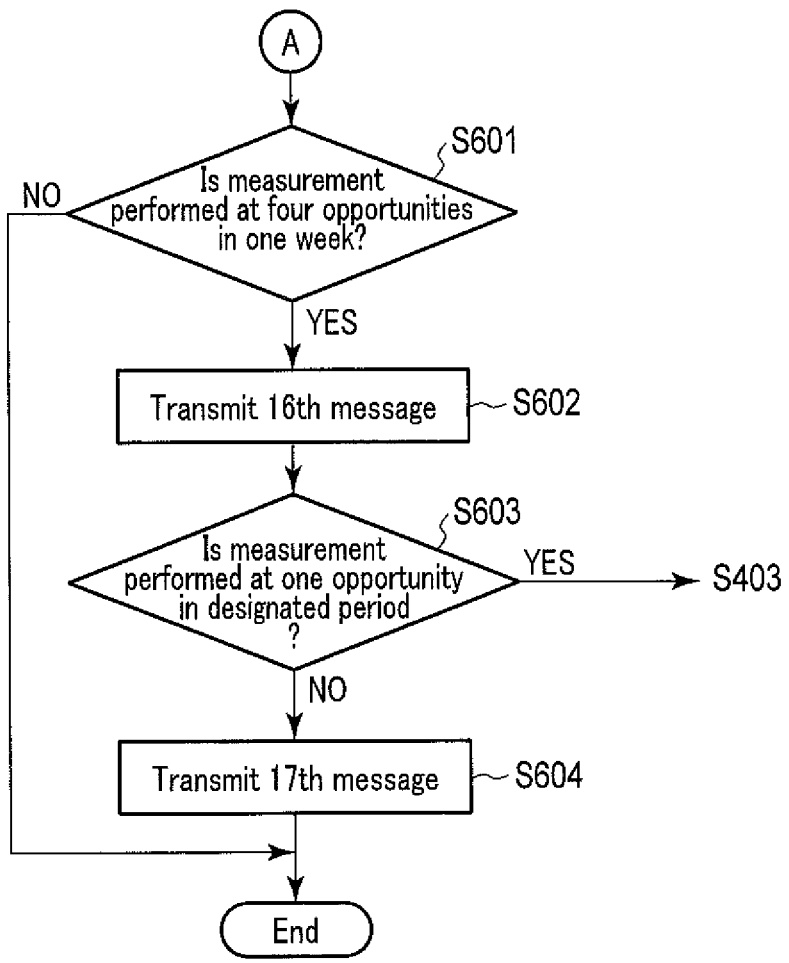
FIG. 13 is a flowchart illustrating an example of a processing procedure of an information processing apparatus according to a second embodiment.

Next, referring to FIG. 13, a description is given of an example of a consultation recommendation operation of the information processing apparatus according to the second embodiment. FIG. 13 is a flowchart illustrating an example of the processing procedure of the information processing system. Note that processing procedures to be described below are merely examples, and each process may be changed as much as possible. Further, in the processing procedures to be described below, omission, replacement and addition of steps can be made as appropriate in accordance with embodiments.

Referring to FIG. 13, a description is given of a part of a consultation recommendation operation which follows "A" in FIG. 10 and relates to the second period. Here, the consultation recommendation operation relating to the second period is, for example, a consultation recommendation operation based on a blood pressure value measured in the daytime.

[Step S601]

If the controller 52 determines the consultation recommendation operation relating to the second period (step S303, NO), the condition determination unit 54 determines whether or not blood pressure measurement was conducted at four opportunities in one week.

Specifically, the condition determination unit 54 determines whether or not there are four pieces of information relating to the second period, which were measured in one week and stored in the information storage unit 53.

If the condition determination unit 54 determines that the blood pressure measurement is not conducted at four opportunities in one week (step S601, NO), the consultation recommendation operation is finished.

[Step S602]

If the condition determination unit 54 determines that the blood pressure measurement is conducted at four opportunities in one week (step S601, YES), the condition determination unit 54 reports this to the message selection unit 55.

The message selection unit 55 selects a 16th message which is to be displayed to the user, when it is determined that the blood pressure measurement is conducted at four opportunities in one week. For example, the 16th message is a message to the effect that "Perform measurement at one more opportunity in one week". This 16th message can be changed as appropriate.

The message transmission unit 57 receives from the message storage unit 56 the 16th message which is selected by the message selection unit 55. Then, the message transmission unit 57 transmits the 16th message to the user (e.g. portable information terminal IT).

Thereby, the user can confirm the 16th message by a freely selected terminal. For example, by viewing the 16th message, the user can understand that the number of times of measurement is deficient in order to execute the consultation recommendation operation. Thus, the user can properly perform the measurement of blood pressure values in order to execute the consultation recommendation operation.

[Step S603]

The condition determination unit 54 determines whether the measurement of the blood pressure value was performed at one more opportunity in a period (designated period) designated in the 16th message.

If the condition determination unit 54 determines that the measurement of the blood pressure value was performed at one opportunity in the designated period (Step S603, YES), the process goes to the operation step S403 described in FIG. 11. Then, the server SV successively performs the operation described in FIG. 11.

[Step S604]

If the condition determination unit 54 determines that the measurement of the blood pressure value is not performed at one opportunity in the designated period (Step S603, NO), the condition determination unit 54 reports this to the message selection unit 55.

The message selection unit 55 selects a 17th message which is to be displayed to the user, when it is determined that the measurement of the blood pressure value is not performed at one opportunity in the designated period. For example, the 17th message is a message to the effect that "Measure the blood pressure at five opportunities from the next week." This 17th message can be changed as appropriate.

The message transmission unit 57 receives from the message storage unit 56 the 17th message which is selected by the message selection unit 55. Then, the message transmission unit 57 transmits the 17th message to the user (e.g. portable information terminal IT).

Thereby, the user can confirm the 17th message by a freely selected terminal. For example, by viewing the 17th message, the user can grasp the number of times of measurement, which is necessary for executing the consultation recommendation operation. Thus, the user can properly perform the measurement of the blood pressure values in order to execute the consultation recommendation operation.

<2-2> Advantageous Effects

According to the JSH Guidelines for the Management of Hypertension 2014, in order to determine hypertension relating to the daytime (e.g. 4:00 AM to 1:59 AM), it is necessary to measure the blood pressure value at five opportunities in one week. However, the user does not necessarily grasp the guidelines. According to the information processing apparatus of the present embodiment, when the consultation recommendation operation is performed, the message to the effect that the blood pressure value needs to be measured at five opportunities in one week is conveyed to the user. As a result, the user can grasp the number of times of measurement, which is necessary for executing the consultation recommendation operation. Thus, the user can properly perform the measurement of blood pressure values in order to execute the consultation recommendation operation.

<3> Third Embodiment

A third embodiment will be described. In the third embodiment, a description is given of another example of the consultation recommendation operation relating to the second period. The basic configuration and basic operation of an information processing apparatus according to the third embodiment are the same as those of the information processing apparatus according to the above-described first embodiment. Accordingly, a description of the matters described in the first embodiment is omitted.

<3-1> Consultation Recommendation Operation

Next, referring to FIG. 14, a description is given of an example of a consultation recommendation operation of the information processing apparatus according to the third embodiment. FIG. 14 is a flowchart illustrating an example of the processing procedure of the information processing system. Note that processing procedures to be described below are merely examples, and each process may be changed as much as possible. Further, in the processing procedures to be described below, omission, replacement and addition of steps can be made as appropriate in accordance with embodiments.

Referring to FIG. 14, a description is given of a part of a consultation recommendation operation which follows "A" in FIG. 10 and relates to the second period. Here, the consultation recommendation operation relating to the second period is, for example, a consultation recommendation operation based on a blood pressure value measured in the daytime.

[Step S701]

If the controller 52 determines the consultation recommendation operation relating to the second period (step S303, NO), the condition determination unit 54 determines whether or not the blood pressure measurement was conducted at S opportunities (S is an arbitrary integer) in one week.

Specifically, the condition determination unit 54 determines whether or not there are S pieces of information relating to the second period, which were measured in one week and stored in the information storage unit 53.

If the condition determination unit 54 determines that the blood pressure measurement is conducted at S opportunities in one week (step S701, YES), the process goes to the operation step S403 described in FIG. 11. Then, the server SV successively performs the operation described in FIG. 11.

[Step S702]

If the condition determination unit 54 determines that the blood pressure measurement is not conducted at S opportunities in one week (step S701, NO), the condition determination unit 54 reports this to the message selection unit 55.

The message selection unit 55 selects an 18th message which is to be displayed to the user, when it is determined that the blood pressure measurement is not conducted at S opportunities in one week. For example, the 18th message is a message to the effect that "Perform measurement at U more opportunity(ies) (U is an integer that is needed to reach S) in one week". This 18th message can be changed as appropriate.

The message transmission unit 57 receives from the message storage unit 56 the 18th message which is selected by the message selection unit 55. Then, the message transmission unit 57 transmits the 18th message to the user (e.g. portable information terminal IT).

Thereby, the user can confirm the 18th message by a freely selected terminal. For example, by viewing the 18th message, the user can understand that the number of times of measurement is deficient in order to execute the consultation recommendation operation. Thus, the user can properly perform the measurement of the blood pressure value in order to execute the consultation recommendation operation.

[Step S703]

The condition determination unit 54 determines whether the measurement of the blood pressure value was performed at S opportunities in total in a period (designated period) designated in the 18th message.

If the condition determination unit 54 determines that the measurement of the blood pressure value was performed at S opportunities in total in the designated period (Step S703, YES), the process goes to the operation step S403 described in FIG. 11. Then, the server SV successively performs the operation described in FIG. 11.

[Step S704]

If the condition determination unit 54 determines that the measurement of the blood pressure value is not performed at S opportunities in total in the designated period (Step S703, NO), the condition determination unit 54 reports this to the message selection unit 55.

The message selection unit 55 selects a 19th message which is to be displayed to the user, when it is determined that the measurement of the blood pressure value is not performed at S opportunities in total in the designated period. For example, the 19th message is a message to the effect that "Measure the blood pressure at S opportunities from the next week." This 19th message can be changed as appropriate.

The message transmission unit 57 receives from the message storage unit 56 the 19th message which is selected by the message selection unit 55. Then, the message transmission unit 57 transmits the 19th message to the user (e.g. portable information terminal IT).

Thereby, the user can confirm the 19th message by a freely selected terminal. For example, by viewing the 19th message, the user can understand the number of times of measurement, which is necessary for executing the consultation recommendation operation. Thus, the user can properly perform the measurement of the blood pressure value in order to execute the consultation recommendation operation.

<3-2> Advantageous Effects

According to the information processing apparatus of the present embodiment, the same advantageous effects as in the above-described second embodiment can be obtained.

<4> Fourth Embodiment

A fourth embodiment will be described. In the fourth embodiment, a description is given of another example of the consultation recommendation operation. The basic configuration and basic operation of an information processing apparatus according to the fourth embodiment are the same as those of the information processing apparatus according to the above-described first embodiment. Accordingly, a description of the matters described in the first embodiment is omitted.

In the present embodiment, for example, a case is described in which if the user transmits biological information to the server SV, the server SV automatically executes a consultation recommendation operation in accordance with the reception of the biological information.

<4-1> Operation

Figure 15:
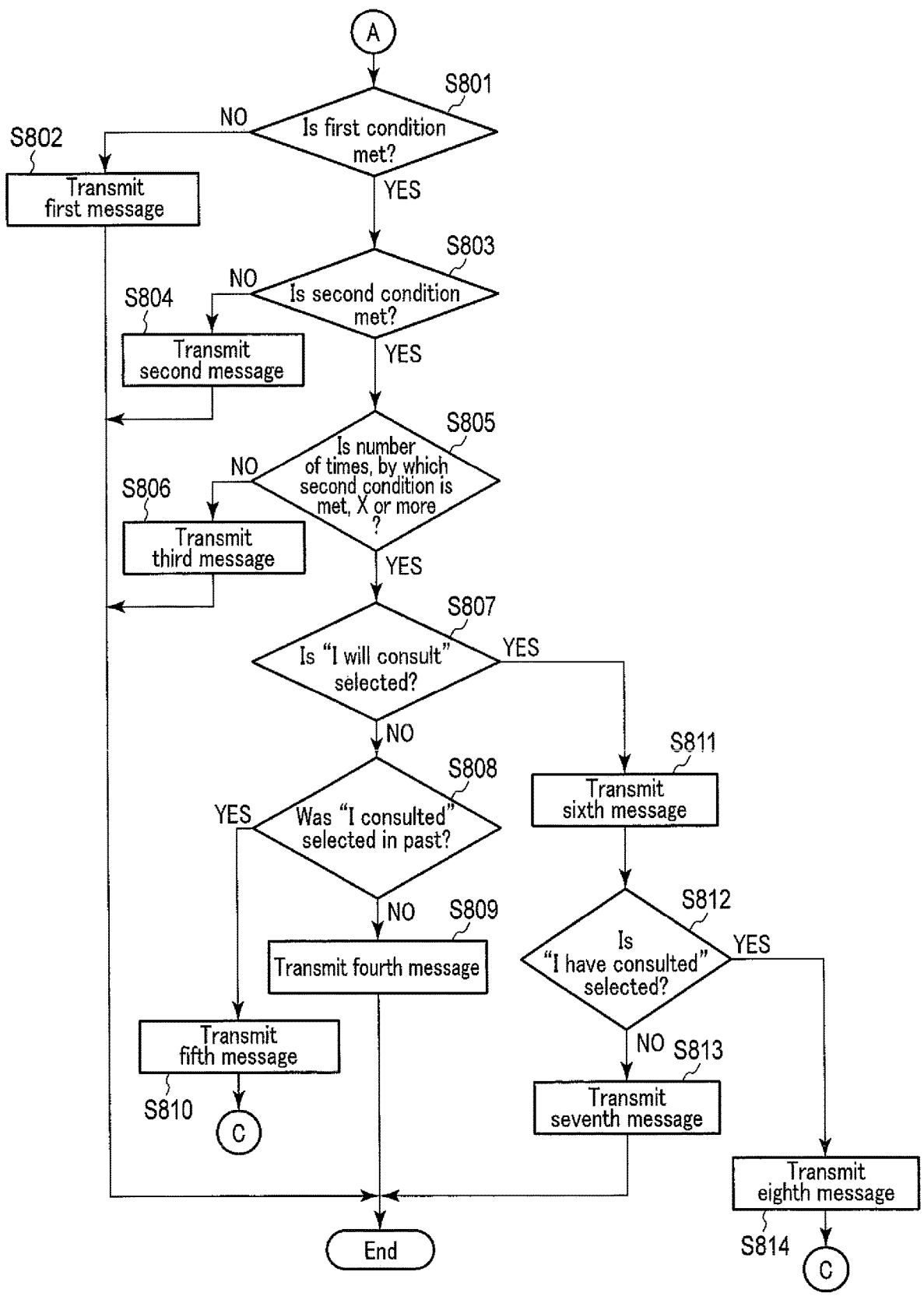
FIG. 15 is a flowchart illustrating an example of a processing procedure of an information processing apparatus according to a fourth embodiment.
Figure 16:
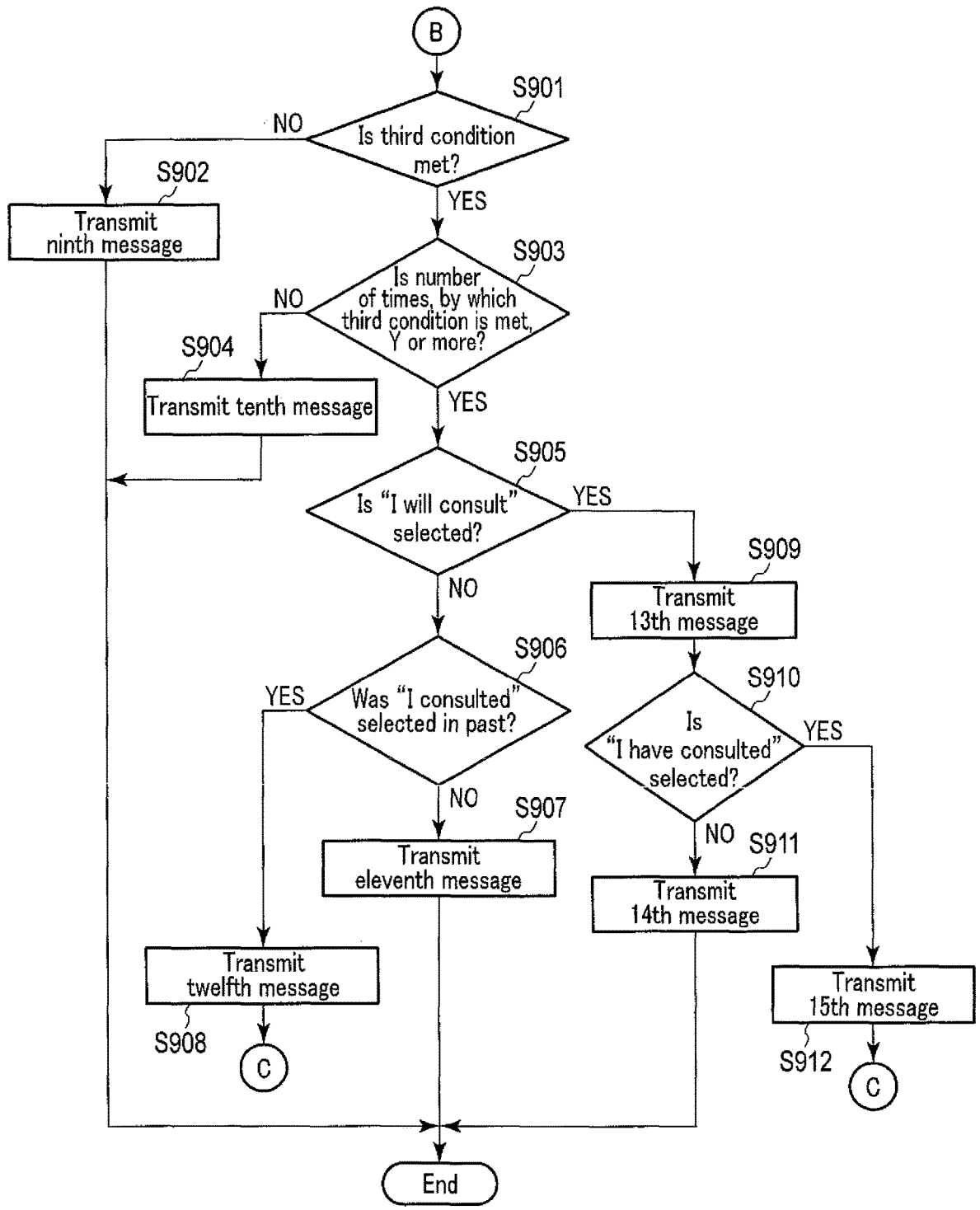
FIG. 16 is a flowchart illustrating an example of the processing procedure of the information processing apparatus according to the fourth embodiment.

Next, referring to FIG. 15 to FIG. 17, a description is given of an example of a consultation recommendation operation of the information processing apparatus according to the fourth embodiment. FIG. 15 to FIG. 17 are flowcharts illustrating an example of the processing procedure of the information processing system. Note that processing procedures to be described below are merely examples, and each process may be changed as much as possible. Further, in the processing procedures to be described below, omission, replacement and addition of steps can be made as appropriate in accordance with embodiments.

To begin with, referring to FIG. 15, a consultation recommendation operation following "A" in FIG. 10, i.e. a consultation recommendation operation relating to the second period, will be described. Here, the consultation recommendation operation relating to the second period is, for example, a consultation recommendation operation based on a blood pressure value measured in the daytime. Since steps S801 to S809 and S811 to S813 are the same as steps S401 to S409 and S411 to S413 described in FIG. 11, a description thereof is omitted.

[Step S810]

Although the basic operation of step S810 is the same as that of step S410 described in FIG. 11, step S810 differs from step S410 of FIG. 11 in that step S1001 of FIG. 17 is executed after the transmission of the fifth message.

[Step S814]

Although the basic operation of step S814 is the same as that of step S414 described in FIG. 11, step S814 differs from step S414 of FIG. 11 in that step S1001 of FIG. 17 is executed after the transmission of the eighth message.

To start with, referring to FIG. 16, a consultation recommendation operation following "B" in FIG. 10, i.e. a consultation recommendation operation relating to the first period, will be described. Here, the consultation recommendation operation relating to the first period is, for example, a consultation recommendation operation based on a blood pressure value measured in the nighttime. Since steps S901 to S907 and S909 to S911 are the same as steps S501 to S507 and S509 to S511 described in FIG. 12, a description thereof is omitted.

[Step S908]

Although the basic operation of step S908 is the same as that of step S508 described in FIG. 12, step S908 differs from step S508 of FIG. 12 in that step S1001 of FIG. 17 is executed after the transmission of the twelfth message.

[Step S912]

Although the basic operation of step S912 is the same as that of step S512 described in FIG. 12, step S912 differs from step S512 of FIG. 12 in that step S1001 of FIG. 17 is executed after the transmission of the 15th message.

Referring to FIG. 17, a description is given of a subsequent part of the consultation recommendation operation, which relates to a subsequent part following "C" in FIG. 15 and a subsequent part following "C" in FIG. 16.

[Step S1001]

The message selection unit 55 selects a 20th message which is to be displayed to the user, after the transmission of the fifth, eighth, twelfth and 16th messages. For example, the 20th method is a message to the effect that "Will the consultation recommendation operation be performed hereafter?". The 20th message can be changed as appropriate.

The message transmission unit 57 receives from the message storage unit 56 the 20th message which is selected by the message selection unit 55. Then, the message transmission unit 57 transmits the 20th message to the user (e.g. portable information terminal IT).

Thereby, the user can confirm the 20th message by a freely selected terminal. If the user makes a response (e.g. selection of "The function of the consultation recommendation operation is to be continued." or "The function of the consultation recommendation operation is not to be continued.") to the 20th message (the message to the effect that "Is the function of the consultation recommendation operation to be continued hereafter?") by a freely selected terminal, the content of the response is reflected in the biological information in the flow described in FIG. 9.

[Step S1002]

The condition determination unit 54 determines whether the response "The function of the consultation recommendation operation is to be continued." is selected as a response result of the 20th message.

[Step S1003]

If the condition determination unit 54 determines that the response "The function of the consultation recommendation operation is to be continued." is selected as the response result of the 20th message (step S1002, YES), the function of the consultation recommendation operation is continued.

Specifically, the server SV automatically executes the consultation recommendation operation upon receiving the biological information.

[Step S1004]

If the condition determination unit 54 determines that the response "The function of the consultation recommendation operation is not to be continued." is selected as the response result of the 20th message (step S1002, NO), the function of the consultation recommendation operation is turned off.

Specifically, the server SV does not automatically execute the consultation recommendation operation even when the server SV receives the biological information.

<4-2> Advantageous Effects

According to the information processing apparatus of the present embodiment, the user can freely turn on/off the consultation recommendation operation.

<5> Fifth Embodiment

A fifth embodiment will be described. In the fifth embodiment, a description is given of another example of the consultation recommendation operation. The basic configuration and basic operation of an information processing apparatus according to the fifth embodiment are the same as those of the information processing apparatuses according to the above-described first to fourth embodiments. Accordingly, a description of the matters described in the first to fourth embodiments is omitted.

In the present embodiment, for example, a case is described in which if the user transmits biological information to the server SV, the server SV automatically executes a consultation recommendation operation in accordance with the reception of the biological information.

<5-1> Operation

Next, referring to FIG. 18, a description is given of an example of a consultation recommendation operation of the information processing apparatus according to the fifth embodiment. FIG. 18 is a flowchart illustrating an example of the processing procedure of the information processing system. Note that processing procedures to be described below are merely examples, and each process may be changed as much as possible. Further, in the processing procedures to be described below, omission, replacement and addition of steps can be made as appropriate in accordance with embodiments.

[Step S1101] & [Step S1102]

The operations in step S1101 and step S1102 are the same as those in step S301 and step S302 of FIG. 10.

[Step S1103]

The condition determination unit 54 determines whether or not the biological information relating to the user is stored in the information storage unit 53.

[Step S1104]

If the condition determination unit 54 determines that the biological information relating to the user is not stored in the information storage unit 53 (step S1103, NO), the condition determination unit 54 reports this to the message selection unit 55.

The message selection unit 55 selects a 21st message which is to be displayed to the user, when the biological information relating to the user is not stored. The 21st message is a message to the effect that "Biological information is not stored." This 21st message can be changed as appropriate.

The message transmission unit 57 receives from the message storage unit 56 the 21st message which is selected by the message selection unit 55. Then, the message transmission unit 57 transmits the 21st message to the user (e.g. portable information terminal IT).

Thereby, the user can confirm the 21st message by a freely selected terminal. For example, by viewing the 21st message, the user can understand that the blood pressure value should be measured.

[Step S1105]

If the condition determination unit 54 determines that the biological information relating to the user is stored in the information storage unit 53 (step S1103, YES), the controller 52 determines whether or not the consultation recommendation operation that is requested is a consultation recommendation operation relating to the first period.

A subsequent consultation recommendation operation is similar to the operations described in the first to fourth embodiments.

<5-2> Advantageous Effects

According to the information processing apparatus of the above-described embodiment, a user, whose biological information is not registered, can be informed of this fact.

<6> Sixth Embodiment

A sixth embodiment will be described. In the six embodiment, a description is given of a message transmission destination registration operation. The basic configuration and basic operation of an information processing apparatus according to the sixth embodiment are the same as those of the information processing apparatuses according to the above-described first to fifth embodiments. Accordingly, a description of the matters described in the first to fifth embodiments is omitted.

<6-1> Message Transmission Destination Registration Operation

In the above-described consultation recommendation operations, the transmission of various messages was described. Here, a method of registering the transmission destination of various messages will be described.

Figure 19:
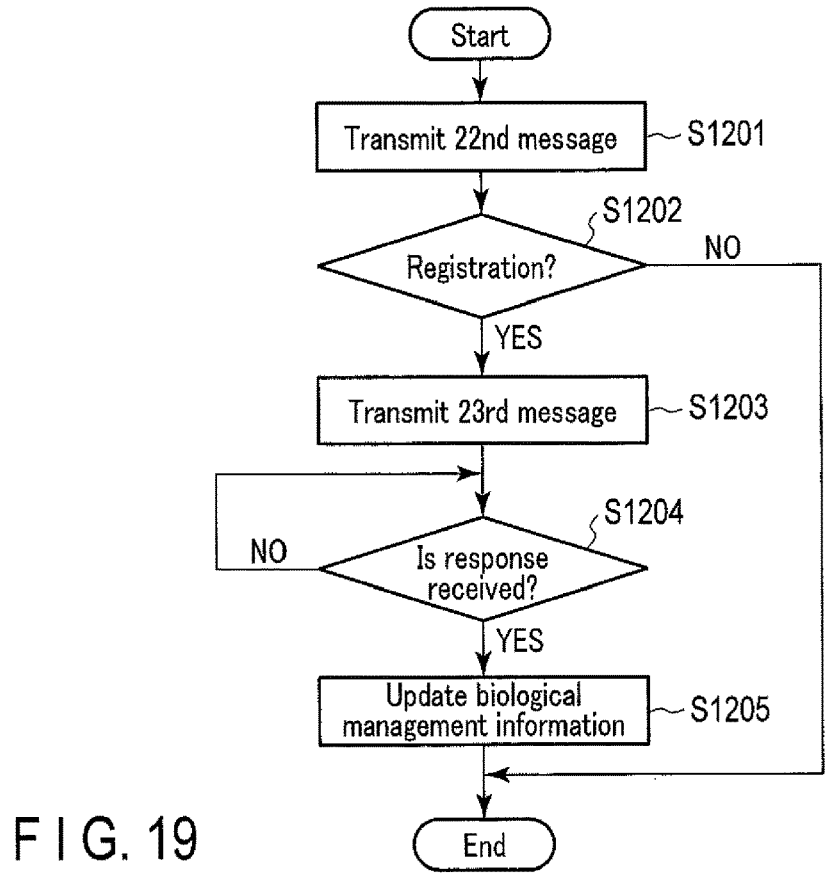
FIG. 19 is a flowchart illustrating an example of a processing procedure of an information processing apparatus according to a sixth embodiment.

Referring to FIG. 19, a description is given of an example of a message transmission destination registration operation of the information processing apparatus according to the sixth embodiment. FIG. 19 is a flowchart illustrating an example of the processing procedure of the information processing apparatus. Note that processing procedures to be described below are merely examples, and each process may be changed as much as possible. Further, in the processing procedures to be described below, omission, replacement and addition of steps can be made as appropriate in accordance with embodiments.

[Step S1201]

The controller 52 transmits, at an arbitrary timing, a message which prompts determination of a transmission destination of messages. Specifically, by an instruction of the controller 52, the message selection unit 55 selects a 22nd message which is to be displayed to the user, when the user is prompted to determine the transmission destination of messages. For example, the 22nd message is a message to the effect that "Will you register the transmission destination of messages?". This 22nd message can be changed as appropriate.

The message transmission unit 57 receives from the message storage unit 56 the 22nd message which is selected by the message selection unit 55. Then, the message transmission unit 57 transmits the 22nd message to the user (e.g. portable information terminal IT).

Thereby, the user can confirm the 22nd message by a freely selected terminal. The user makes a response (e.g. selection of "I will register." or "I will not register.") to the 22nd message (the message to the effect that "Will you register the transmission destination of messages?") by a freely selected terminal.

[Step S1202]

The condition determination unit 54 determines whether or not a response to the effect that "I will register the transmission destination of messages." is selected as a response result of the 22nd message.

If the condition determination unit 54 determines that the response to the effect that "I will register the transmission destination of messages." is not selected as the response result of the 22nd message (step S1202, NO), the message transmission registration operation is finished.

[Step S1203]

If the condition determination unit 54 determines that the response to the effect that "I will register the transmission destination of messages." is selected as the response result of the 22nd message (step S1202, YES), the condition determination unit 54 reports this to the message selection unit 55.

The message selection unit 55 selects a 23rd message which is to be displayed to the user, when the response to the effect that "I will register the transmission destination of messages." is selected. For example, the 23rd message is a message to the effect that "Write the destination to be registered." This 23rd message can be changed as appropriate.

The message transmission unit 57 receives from the message storage unit 56 the 23rd message which is selected by the message selection unit 55. Then, the message transmission unit 57 transmits the 23rd message to the user (e.g. portable information terminal IT).

Thereby, the user can confirm the 23rd message by a freely selected terminal. The user makes a response (e.g. the mail address, the name, the telephone number, the relation to the user, etc.) to the 23rd message (the message to the effect that "Write the destination to be registered.") by a freely selected terminal.

[Step S1204]

The condition determination unit 54 determines whether the response result of the 23rd message is received or not.

[Step S1205]

If the condition determination unit 54 determines that the response result of the 23rd message is received (Step S1204, YES), the controller 52 reflects the response result of the 23rd message in the biological management information, and updates the biological management information of the information storage unit 53.

In the manner as described above, the message transmission destination registration operation is finished.

Note that the above-described message transmission destination registration operation may be performed on a message-by-message basis.

<6-2> Advantageous Effects

According to the information processing apparatus of the above-described embodiment, the transmission destination of messages can be freely determined. Thus, not only the user but also a family member or the like of the user can know the information relating to the consultation recommendation operation of the user. Thus, the user's health condition can be observed in cooperation with the user's family or the like.

<7> Seventh Embodiment

A seventh embodiment will be described. In the seventh embodiment, a description is given of an operation of changing a message, which is to be sent, in accordance with the transmission destination which is registered in the biological management information. The basic configuration and basic operation of an information processing apparatus according to the seventh embodiment are the same as those of the information processing apparatuses according to the above-described first to sixth embodiments. Accordingly, a description of the matters described in the first to sixth embodiments is omitted.

<7-1> Message Transmission Operation

In the above-described sixth embodiment, the method of registering the transmission destination of various messages was described. In the first to fourth embodiments, the server SV may change the message that is to be transmitted, in accordance with the transmission destination registered in the biological management information. Here, a description is given of a method of changing the message that is to be transmitted, in accordance with the transmission destination registered in the biological management information.

Figure 20:
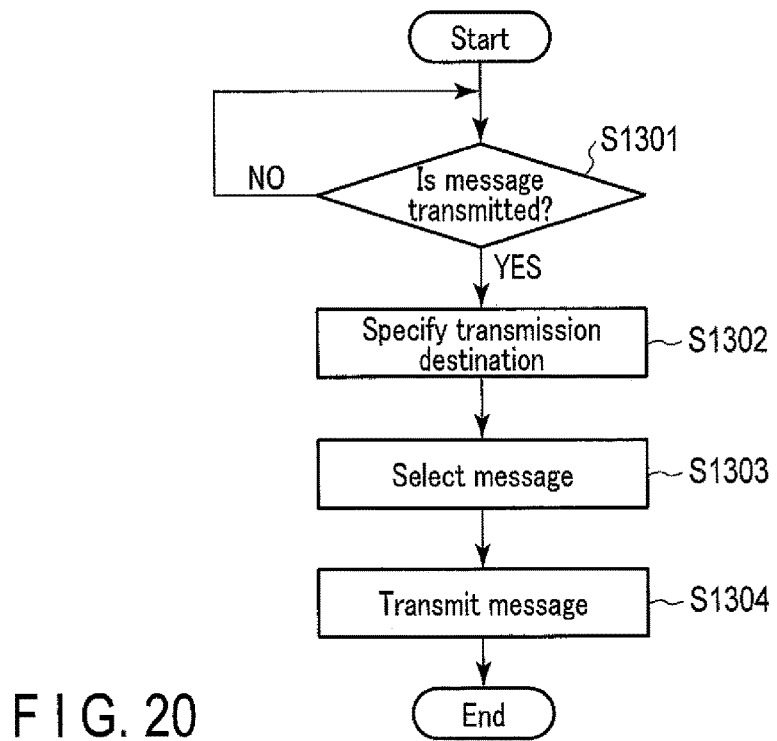
FIG. 20 is a flowchart illustrating an example of a processing procedure of an information processing apparatus according to a seventh embodiment.

Referring to FIG. 20, a message transmission operation is described. The message transmission operation is a more specific operation example of each message transmission operation in the above-described first to fourth embodiments. FIG. 20 is a flowchart illustrating an example of the processing procedure of the information processing apparatus. Note that processing procedures to be described below are merely examples, and each process may be changed as much as possible. Further, in the processing procedures to be described below, omission, replacement and addition of steps can be made as appropriate in accordance with embodiments.

[Step S1301]

The server SV determines whether or not to transmit a message. Specifically, for example, the condition determination unit 54 determines whether or not to select a message.

[Step S1302]

When it is determined that the message is to be transmitted (step S1301, YES), the condition determination unit 54 specifies the transmission destination of the message. The transmission destination of the message is registered in the biological management information of the information storage unit 53. Thus, by referring to the biological management information, the condition determination unit 54 can specify the transmission destination of the message.

[Step S1303]

The message selection unit 55 selects a message, based on the transmission destination of the message.

Here, a concrete example is described in brief. For example, in step S402 in FIG. 11, the message to the effect that "Since the first condition is not met, the consultation recommendation operation cannot be executed." is selected for the user. However, a message to the effect that "Although the user tried to execute the consultation recommendation operation, the consultation recommendation operation could not be executed since the first condition fails to be met. Please inform the user that the first condition should be met." is selected for a transmission destination (for example, the family) other than the user.

[Step S1304]

The message transmission unit 57 receives from the message storage unit 56 the message which is selected by the message selection unit 55. Then, the message transmission unit 57 transmits the message which corresponds to the transmission destination.

<7-2> Advantageous Effects

According to the information processing apparatus of the above-described embodiment, the message can be changed in accordance with each of the transmission destinations of messages. Thereby, a proper message can be transmitted to each transmission destination.

For example, if an identical message is sent to all transmission destinations which are registered, it is possible that persons other than the user are confused. For example, in step S1302, the case was described that the message to the effect that "Since the first condition is not met, the consultation recommendation operation cannot be executed." is selected for the user, and the message to the effect that "Although the user tried to execute the consultation recommendation operation, the consultation recommendation operation could not be executed since the first condition fails to be met. Please inform the user that the first condition should be met." is selected for a transmission destination (for example, the family) other than the user.

However, if the message to the effect that "Since the first condition is not met, the consultation recommendation operation cannot be executed." is also selected for a transmission destination (for example, the family) other than the user, a person other than the user cannot understand "who cannot execute the consultation recommendation operation".

According to the information processing apparatus of the above-described embodiment, however, this problem can be avoided since a proper message is transmitted to each transmission destination.

<8> Eighth Embodiment

An eighth embodiment will be described. In the eighth embodiment, a description is given of an operation of changing a frequency of transmission of a message in accordance with the transmission destination which is registered in the biological management information. The basic configuration and basic operation of an information processing apparatus according to the eighth embodiment are the same as those of the information processing apparatuses according to the above-described first to seventh embodiments. Accordingly, a description of the matters described in the first to seventh embodiments is omitted.

<8-1> Message Transmission Operation

In the above-described sixth embodiment, the method of registering the transmission destination of various messages was described. In the first to fourth embodiments, the server SV may change the frequency of transmission of a message in accordance with the transmission destination registered in the biological management information. Here, a description is given of a method of changing the frequency of transmission of a message in accordance with the transmission destination registered in the biological management information.

Figure 21:
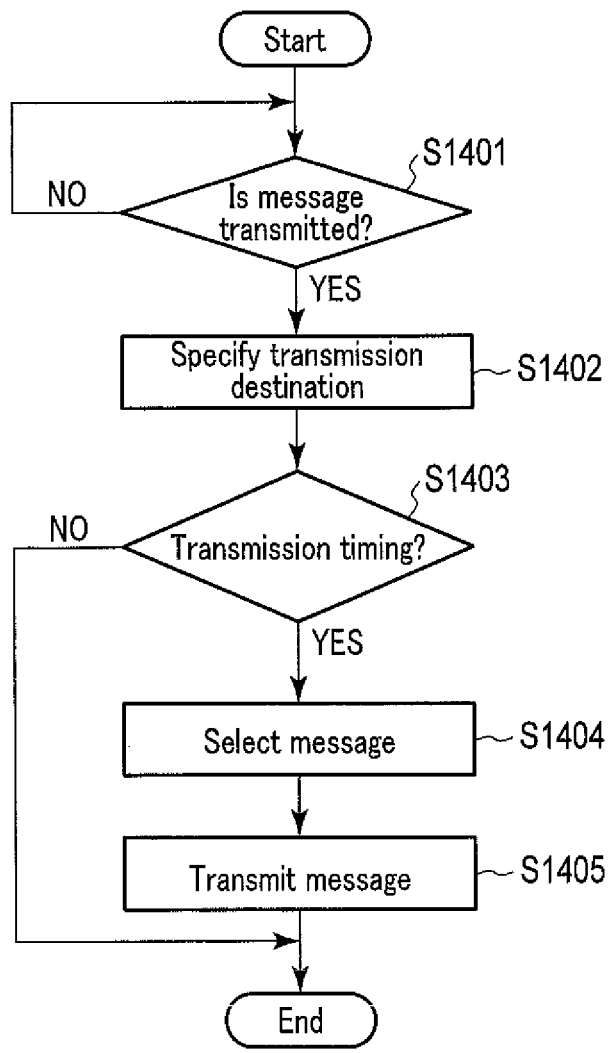
FIG. 21 is a flowchart illustrating an example of a processing procedure of an information processing apparatus according to an eighth embodiment.

Referring to FIG. 21, a message transmission operation is described. The message transmission operation is a more specific operation example of each message transmission operation in the above-described first to fourth embodiments. FIG. 21 is a flowchart illustrating an example of the processing procedure of the information processing apparatus. Note that processing procedures to be described below are merely examples, and each process may be changed as much as possible. Further, in the processing procedures to be described below, omission, replacement and addition of steps can be made as appropriate in accordance with embodiments.

[Step S1401]

The server SV determines whether or not to transmit a message. Specifically, for example, the condition determination unit 54 determines whether or not to select a message.

[Step S1402]

When it is determined that the message is to be transmitted (step S1401, YES), the condition determination unit 54 specifies the transmission destination of the message.

[Step S1403]

The condition determination unit 54 determines whether or not a transmission timing has come with respect to each of transmission destinations of messages. The transmission timing is stored, for example, in the memory 41b or storage unit 42 of the server SV. In addition, the transmission timing can be changed as appropriate.

If the condition determination unit 54 determines that the transmission timing has not come (step S1403, NO), the message transmission operation is finished with respect to the transmission destination of the message.

[Step S1404]

If the condition determination unit 54 determines that the transmission timing has come (step S1403, YES), the condition determination unit 54 reports this to the message selection unit 55.

The message selection unit 55 selects a message, based on the transmission destination of the message.

[Step S1405]

The message storage unit 56 transmits the message, which is selected by the message selection unit 55, to the transmission destination via the message transmission unit 57.

<8-2> Advantageous Effects

According to the information processing apparatus of the above-described embodiment, the frequency of transmission of messages can be changed with respect to each of transmission destinations of messages. Thereby, a proper message can be transmitted to each transmission destination.

For example, if messages are transmitted, with an identical frequency, to all registered transmission destinations, messages are transmitted unnecessarily to a person other than the user. For example, it should suffice if a person other than the user grasps the status of the user's consultation recommendation operation about once in a week.

According to the information processing apparatus of the above-described embodiment, this problem can be avoided since messages are transmitted to each transmission destination with a proper frequency.

<9> Modifications

In each of the above-described embodiments, the server SV was described as one example of the "information processing apparatus IPE" of the application example. However, the "information processing apparatus IPE" of the application example is not limited to the server SV, and may be the blood pressure monitor BT, portable information terminal IT, doctor terminal DT, or the like. In addition, the structural elements of the information processing apparatus IPE may be distributatively arranged in the server SV, blood pressure monitor BT, portable information terminal IT and doctor terminal DT.

For example, a brief description is given of the case in which the "information processing apparatus IPE" of the application example is realized by the portable information terminal IT. The controller 21 of the portable information terminal IT loads the program, which is stored in the storage unit 22, into the memory 21b. Then, the controller 21 interprets and executes, by the processor 21a, the program loaded in the memory 21b, thereby realizing the above-described functional configuration.

In addition, a brief description is given of the case in which the "information processing apparatus IPE" of the application example is realized by the doctor terminal DT. The controller 31 of the doctor terminal DT loads the program, which is stored in the storage unit 32, into the memory 31b. Then, the controller 31 interprets and executes, by the processor 31a, the program loaded in the memory 31b, thereby realizing the above-described functional configuration.

Besides, in each of the above-described embodiments, various conditions, etc. are determined based on the JSH Guidelines for the Management of Hypertension 2014. However, aside from this, the conditions in the above-described embodiments may be changed if the JSH Guidelines for the Management of Hypertension are updated, and the conditions in the embodiments may be changed by doctors and the like.

The present invention is not limited directly to the above-described embodiments. In practice, the structural elements can be modified and embodied without departing from the spirit of the invention. Various inventions can be made by properly combining the structural elements disclosed in the embodiments. For example, some structural elements may be omitted from all the structural elements disclosed in the embodiments. Furthermore, structural elements in different embodiments may properly be combined.

What is claimed is:

1. An information processing apparatus, the apparatus comprising a processor being configured to:
    determine, when a biological information of a measurement subject is received, whether the biological information is a first biological information relating to a blood pressure value being measured in a daytime or a second biological information relating to a blood pressure value being measured in a nighttime;
    determine, when the biological information is the first biological information, whether or not a blood pressure measurement is conducted a predetermined number of times in a period;
    select a first message which indicates a deficiency of the number of times of the blood pressure measurement when the blood pressure measurement is not conducted for the predetermined number of times;
    determine, when the biological information is the first biological information, and when the blood pressure measurement is conducted for the predetermined number of times, whether or not the first biological information meets a first condition;
    determine, when the first biological information meets the first condition, whether or not a number of times, by which the first biological information meets the first condition, exceeds a first value;

select a second message which recommends a consultation to a medical institution when the first value is not exceeded;

select a third message which confirms a presence or an absence of a consultation in the medical institution when the first value is exceeded;

determine, when the biological information is the second biological information, whether or not the second biological information meets a second condition different from the first condition;

determine, when the second biological information meets the second condition, whether or not a number of times, by which the second biological information meets the second condition, exceeds a second value;

select a fourth message which recommends a consultation to a medical specialist or a lifestyle-related disease certified physician when the second value is not exceeded; and select a fifth message which confirms a presence or an absence of a consultation of the medical specialist or the lifestyle-related disease certified physician when the second value is exceeded.

2. The information processing apparatus of claim 1, wherein
the first biological information includes an average value of blood pressure values in at least five days in one week, the blood pressure being measured at one or more opportunities in each of the five days, and
the second biological information includes an average value of blood pressures measured at least at one opportunity in one week.

3. The information processing apparatus of claim 1, wherein
the determining as to whether or not the first condition is met includes, at least, determining whether or not a systolic blood pressure value included in the first biological information is a third value or more, or whether or not a diastolic blood pressure value included in the first biological information is a fourth value or more, and
the determining as to whether or not the second condition is met includes, at least, determining whether or not a systolic blood pressure value included in the second biological information is a fifth value or more, or whether or not a diastolic blood pressure value included in the second biological information is a sixth value or more.

4. The information processing apparatus of claim 1, wherein the apparatus is configured to cause a device, which supplies the first biological information or the second biological information, to display the selected message.

5. The information processing apparatus of claim 1, the apparatus further comprising:
a storage unit configured to store the first biological information and the second biological information.

6. The information processing apparatus of claim 1, the processor being further configured to:
select, when the first biological information does not meet the first condition, a seventh message indicating that a consultation to a medical institution is unnecessary; and
select, when the second biological information does not meet the second condition, an eighth message indicating that a consultation to a medical institution is unnecessary.

7. The information processing apparatus of claim 1, wherein
the first condition, the second condition, the first value, and the second value are based on a guideline for management of hypertension.

8. A non-transitory computer readable medium storing a computer program for causing a computer to function as the information processing apparatus of claim 1.

9. The information processing apparatus of claim 1, the processor being further configured to:
select a sixth message which recommends a consultation to the medical specialist or the lifestyle-related disease certified physician when the consultation of the medical specialist or the lifestyle-related disease certified physician is absent.

10. An information processing method which is executed by an apparatus configured to process a blood pressure value measured by a blood pressure measuring unit, the method comprising:
determining, when a biological information of a measurement subject is received, whether the biological information is a first biological information relating to a blood pressure value being measured in a daytime or a second biological information relating to a blood pressure value being measured in a nighttime;
determining, when the biological information is the first biological information, whether or not a blood pressure measurement is conducted a predetermined number of times in a period;
selecting a first message which indicates a deficiency of the number of times of the blood pressure measurement when the blood pressure measurement is not conducted for the predetermined number of times;
determining, when the biological information is the first biological information and when the blood pressure measurement is conducted for the predetermined number of times, whether or not the first biological information meets a first condition;
determining, when the first biological information meets the first condition, whether or not a number of times, by which the first biological information meets the first condition, exceeds a first value;
selecting a second message which recommends a consultation to a medical institution when the first value is not exceeded;
selecting a third message which confirms a presence or an absence of a consultation in the medical institution when the first value is exceeded;
determining, when the biological information is the second biological information, whether or not the second biological information meets a second condition different from the first condition;
determining, when the second biological information meets the second condition, whether or not a number of times, by which the second biological information meets the second condition, exceeds a second value;
selecting a fourth message which recommends a consultation to a medical specialist or a lifestyle-related disease certified physician when the second value is not exceeded; and
selecting a fifth message which confirms a presence or an absence of a consultation of the medical specialist or the lifestyle-related disease certified physician when the second value is exceeded.

11. The information processing method of claim 10, further comprising:

selecting a sixth message which recommends a consultation to the medical specialist or the lifestyle-related disease certified physician when the consultation of the medical specialist or the lifestyle-related disease certified physician is absent.

12. The information processing method of claim 10, further comprising:

selecting, when the first biological information does not meet the first condition, a seventh message indicating that a consultation to a medical institution is unnecessary; and selecting, when the second biological information does not meet the second condition, an eighth message indicating that a consultation to a medical institution is unnecessary.

\* \* \* \* \*